United States Patent
Archibald et al.

(10) Patent No.: US 6,329,362 B1
(45) Date of Patent: Dec. 11, 2001

(54) CINNAMIC ACID DERIVATIVES

(75) Inventors: Sarah Catherine Archibald; John Clifford Head, both of Maidenhead; Graham John Warrellow, Northwood; John Robert Porter, Chinnor, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/270,408

(22) Filed: Mar. 16, 1999

(30) Foreign Application Priority Data

Mar. 16, 1998 (GB) .................................................. 9805655

(51) Int. Cl.$^7$ ........................ A61K 31/03; C07C 229/00; C07D 213/44

(52) U.S. Cl. ..................... 514/188; 514/423; 514/647; 514/826; 514/858; 514/863; 514/866; 514/885; 514/886; 514/887; 546/262; 548/530; 560/19; 562/433

(58) Field of Search ............................. 546/262; 514/423, 514/144, 506, 521, 523, 647, 858, 826, 863, 886, 887; 548/530; 560/19, 8, 9, 16, 21, 23, 51, 55, 76, 81, 95; 562/433, 405, 442, 445, 465, 471, 472, 480, 489

(56) References Cited

U.S. PATENT DOCUMENTS

| | | | |
|---|---|---|---|
| 4,554,273 | 11/1985 | Bayssat et al. | 514/221 |
| 4,987,132 | 1/1991 | Mase et al. | 514/252 |
| 5,164,372 | 11/1992 | Matsuo et al. | 514/19 |
| 5,227,490 | 7/1993 | Hartman et al. | . |
| 5,260,277 | 11/1993 | McKenzie | 544/18 |
| 5,296,486 | 3/1994 | Lazer et al. | 514/333 |
| 5,360,815 | * 11/1994 | Fortin et al. | . |
| 5,399,585 | 3/1995 | Alig et al. | 514/438 |
| 5,510,346 | 4/1996 | Martin et al. | 514/221 |
| 5,698,691 | 12/1997 | Yukimasa et al. | 540/490 |
| 5,773,646 | 6/1998 | Michael et al. | . |
| 6,093,696 | 7/2000 | Head et al. | 514/19 |

FOREIGN PATENT DOCUMENTS

| | | |
|---|---|---|
| 23 16 881 A | 10/1973 | (DE) . |
| 28 37 264 A1 | 3/1979 | (DE) . |
| 196 54 483 A | 1/1998 | (DE) . |
| 0 031 104 A1 | 7/1981 | (EP) . |
| 0 048 763 A1 | 4/1982 | (EP) . |
| 0 144 230 A | 6/1985 | (EP) . |
| 0 322 068 A1 | 6/1989 | (EP) . |
| 0 394 989 A2 | 10/1990 | (EP) . |
| 0 498 268 A2 | 8/1992 | (EP) . |
| 0 596 406 A1 | 5/1994 | (EP) . |
| 0 710 657 A1 | 5/1996 | (EP) . |
| 0 710 659 A1 | 5/1996 | (EP) . |
| 0 842 943 A2 | 5/1998 | (EP) . |
| 0 842 945 A2 | 5/1998 | (EP) . |
| 56 090045 | 7/1981 | (JP) . |
| 03 135962 | 6/1991 | (JP) . |

(List continued on next page.)

OTHER PUBLICATIONS

Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.

Numani, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Rico, J.G., et al., "Highly stereoselective michael addition to an α,β–unsaturated ester as the crucial step in the synthesis of a novel β–amino acid–containing fibrinogen receptor antagonist," *J. Org. Chem.*, 1993, 58, 7948–7951.

(List continued on next page.)

*Primary Examiner*—Paul J. Killos
*Assistant Examiner*—Robert W. Deemie
(74) *Attorney, Agent, or Firm*—Woodcock Washburn Kurtz Mackiewicz & Norris LLP

(57) ABSTRACT

Compounds of formula (1) are described:

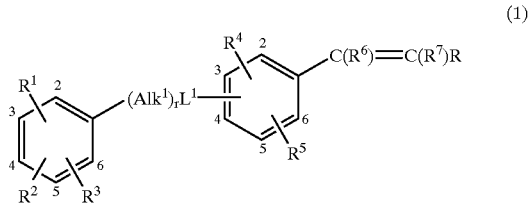

wherein $L^1$ is a covalent bond or a linker atom or group;

R is a carboxylic acid (—$CO_2H$) or a derivative threof;

$R^6$ and $R^7$ which may be the same or different is each an atom or group —$L^2(Alk^2)_tL^3R^{12}$ in which $L^2$, $L^3$, $Alk^2$ and t are as previously defined and $R^{12}$ is a hydrogen or halogen atom or an —$OR^9$, —$NR^9R^{10}$, —$NO_2$, —CN, —$CO_2R^9$, —$CONR^9R^{10}$, —$COR^9$, —$N(R^9)COR^{10}$, —$N(R^9)CSR^{10}$, —$SO_2N(R^9)(R^{10})$, —$N(R^9)SO_2R^9$, —$N(R^9)CON(R^{10})(R^{11})$, —$N(R^9)CSN(R^{10})(R^{11})$, —$N(R^9)SO_2N(R^{10})(R^{11})$, or an optionally substituted aliphatic, heteroaliphatic, cycloaliphatic, heterocycloaliphatic, aromatic or heteroaromatic group provided that $R^6$ and $R^7$ are not both hydrogen atoms and when $R^7$ is a hydrogen atom then $R^4$ and $R^5$ is each a hydrogen or halogen atom or an alkyl, alkoxy or nitro group; and the salts, solvates, hydrates and N-oxides thereof, for use in modulating cell adhesion.

The compounds are able to inhibit the binding of alpha 4 integrins to their ligands and are of use in the prophylaxis and treatment of immune or inflammatory disorders.

16 Claims, No Drawings

FOREIGN PATENT DOCUMENTS

| | | |
|---|---|---|
| WO 86/02353 | 4/1986 | (WO) . |
| WO 93/00095 | 1/1993 | (WO) . |
| WO 93/08174 | 4/1993 | (WO) . |
| WO 93/09795 | 5/1993 | (WO) . |
| WO 94/15954 | 7/1994 | (WO) . |
| WO 94/15955 | 7/1994 | (WO) . |
| WO 94/29285 | 12/1994 | (WO) . |
| WO 95/13811 | 5/1995 | (WO) . |
| WO 95/15973 | 6/1995 | (WO) . |
| WO 95/19356 | 7/1995 | (WO) . |
| WO 95/35314 | 12/1995 | (WO) . |
| WO 96/01644 | 1/1996 | (WO) . |
| WO 96/22966 | 8/1996 | (WO) . |
| WO 96/26190 | 8/1996 | (WO) . |
| WO 97/03094 | 1/1997 | (WO) . |
| WO 97/12866 | 4/1997 | (WO) . |
| WO 97/23480 | 7/1997 | (WO) . |
| WO 97/24124 | 7/1997 | (WO) . |
| WO 97/31907 | 9/1997 | (WO) . |
| WO 97/36858 | 10/1997 | (WO) . |
| WO 97/36859 | 10/1997 | (WO) . |
| WO 97/36861 | 10/1997 | (WO) . |
| WO 97/36862 | 10/1997 | (WO) . |
| WO 97/44333 | 11/1997 | (WO) . |
| WO 97/47618 | 12/1997 | (WO) . |
| WO 98/00395 | 1/1998 | (WO) . |
| WO 97/04247 | 2/1998 | (WO) . |
| WO 98/04247 | 2/1998 | (WO) . |
| WO 98/04913 | 2/1998 | (WO) . |
| WO 98/18460 | 5/1998 | (WO) . |
| WO 98/25892 | 6/1998 | (WO) . |
| WO 98/31359 | 7/1998 | (WO) . |
| WO 98/42662 | 10/1998 | (WO) . |
| WO 98/54207 | 12/1998 | (WO) . |
| WO 99/20272 | 4/1999 | (WO) . |
| WO 99/26921 | 6/1999 | (WO) . |
| WO 99/26922 | 6/1999 | (WO) . |
| WO 99/26945 | 6/1999 | (WO) . |
| WO 99/30799 | 6/1999 | (WO) . |
| WO 99/31061 | 6/1999 | (WO) . |
| WO 99/31099 | 6/1999 | (WO) . |
| WO 99/32457 | 7/1999 | (WO) . |
| WO 99/35163 | 7/1999 | (WO) . |
| WO 99/36393 | 7/1999 | (WO) . |
| WO 99/37618 | 7/1999 | (WO) . |
| WO 99/43642 | 9/1999 | (WO) . |
| WO 99/44994 | 9/1999 | (WO) . |
| WO 99/48879 | 9/1999 | (WO) . |
| WO 99/52879 | 10/1999 | (WO) . |
| WO 99/52896 | 10/1999 | (WO) . |
| WO 99/52898 | 10/1999 | (WO) . |
| WO 99/60015 | 11/1999 | (WO) . |
| WO 99/61465 | 12/1999 | (WO) . |
| WO 99/64395 | 12/1999 | (WO) . |
| WO 99/67230 | 12/1999 | (WO) . |
| WO 00/00486 | 1/2000 | (WO) . |
| WO 00/01383 | 1/2000 | (WO) . |
| WO 00/06169 | 2/2000 | (WO) . |
| WO 00/07544 | 2/2000 | (WO) . |
| WO 00/17197 | 3/2000 | (WO) . |
| WO 00/23419 | 4/2000 | (WO) . |
| WO 00/31067 | 6/2000 | (WO) . |
| WO 00/35855 | 6/2000 | (WO) . |

OTHER PUBLICATIONS

Shimohigashi, Y., et al., "Dehydro–enkephalins," *Int. J. Peptide Protein Res.*, 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Zablocki, J.A., et al., "Potent in Vitro and in Vivo inhibitors of platelet aggregation based upon the arg–gly–asp sequence of fibrinogen. (Aminobenzamidino) succinyl (ABAS) series of orally active fibrinogen receptor antagonist," *J. Med. Chem.*, 1995, 38, 2378–2394.

Alhaique, F., et al., "Cyclisation of dinitriles by sodium alkoxides a new synthesis of napthyridines," *Tetrahedron Letters*, 1975, 3, 173–174.

Ames, D.E., et al., "Condensation of $\beta$–dicarbonyl compounds with halogenopyridinecarb–oxylic acids. A convenient synthesis of some naphthyridine derivates," *J.C.S. Perkins I*, 1972, 705–710.

Bodor, N., "Novel approaches in prodrug design," *Alfred Benzon Symposium*, 1982, 17, 156–177.

Brooks, Peter C., "Antiintegrin $\alpha v \beta 3$ blocks human breast cancer growth and angiogenesis in human skin," *J. Clin. Invest.*, 1995, 96, 1815–1822.

Hodivala–Dilke, K.M., "$\beta 3$–integrin–deficient mice are a model for glanzmann thrombasthenia showing placental defects and reduced survival," *J. Clin. Invest.*, 1999, 103(2), 229–238.

Davies, S..G., et al., "Asymmetric synthesis of R–$\beta$–amino butanoic and S–$\beta$–tyrosine: homochiral lithium amide equivalents for Michael additions to$\alpha,\beta$–unsaturated esters," *Tetra. Asymmetry*, 1991, 2(3), 183–186.

Erle, D.J., et al., "Expression and function of the Mad-CAM–1 receptor, integrin $\alpha 4\beta 7$, on human leukocytes," *J. Immunol.*, 1994, 153, 517–528.

Giacomello, et al., "Synthesis of 2,6–naphthyridine," *Tetra. Letters*, 1965, 16, 1117–1121.

Hammes, H., et al., "Subcutaneous injection of a cyclic peptide antagonist of vitronectin receptor–type integrins inhibits retinal neovascularization," *Nature Medicine*, 1996, 2, 529–533.

Hodivala–Dilke, K.M.,"$\beta 3$–integrin–deficient mice are a model for glanzmann thrombasthenia showing placental defects and reduced survival," *J. Clin. Invest.*, 1999, 103(2), 229–238.

Kalvin, D.M., et al., Synthesis of (4R)–D,L–[4–$^2$H]–and (4S)–D,L–[4–$^2$H] homoserine lactones, *J. Org. Chem.*, 1985, 50, 2259–2263.

Koivunen, E., et al., "Selection of peptides binding to the $\alpha_5\beta_1$ integrin from phage display library," *J. Biological Chemistry*, 1993, 268(27), 20205–20210.

Mitjans, F., et al., "An anti–$\alpha v$–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.

Newham, P., et al., "Integrin adhesion receptors: structure, function and implications for biomedicine," *Nolecular Medicine Today*, 1996, 304–313.

Numata, A., et al., "General synthetic method for naphthyridines and their N–oxides containing isoquinolinic nitrogen," *Synthesis*, 1999, 2, 306–311.

Sakamoto, T., et al., "Condensed heteroaromatic ring systems, III. synthesis of naphthyridine derivatives by cyclization of ethynylpyridinecarboxamides," *Chem. Pharm. Bull.* 1985, 33(2), 626–633.

Singh, G., et al., "Prodrug approach in new drug design and development," *J. Sci. Ind. Res.*, 1996, 55, 497–510.

Srivatsa, S.S., et al., "Selective $\alpha v\beta 3$ integrin blockade potently limits neointimal hyperplasia and lumen stenosis following deep coronary arterial stent injury: evidence for the functional importance of integrin $\alpha v\beta 3$ and osteopontin expression during neointima formation," *Cariovascular Research*, 1997, 36, 408–428.

Stupack, D.G., et al., "induction of $\alpha_v \beta_3$ integrin–mediated attachment to extracellular matrix in $\beta_1$ integrin (CD29)–negative B cell lines," *Experi. Cell Research*, 1992, 203, 443–448.

Tan R., et al., "Synthesis of 2, 6–naphthyridine and some of its derivatives," *Tetrahedron Letters*, 1965, 31, 2737–2744.

Abraham, W.M. et al., "$\alpha_4$–Integrins Mediate Antigen–Induced Late Bronchial Responses and Prolonged Airway Hyperresponsiveness in Sheep", *J. Clin. Invest.*, 1994, 93, 776–787.

Berlin, C. et al., "$\alpha 4\beta 7$ Integrin Mediates Lymphocyte Binding to the Mucosal Vascular Addressin MAdCAM–1", *Cell*, 1993, 74, 185–195.

Binns, R.M. et al., "The Role of E–Selection in Lymphocyte and Polymorphonuclear Cell Recruitment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$",*J. Immunol.*, 1996, 156, 719–726.

Cardarelli, P.M. et al., "Cyclic RGD Peptide Inhibits $\alpha 4\beta 7$ Interaction with Connecting Segment 1 and Vascular Cell Adhesion Molecule", *J. Biol. Chem.*, 1994, 269(28), 18668–18673.

Corey, E.J. et al., "A Synthetic Method for Formyl $\rightarrow$ Ethynyl Conversion (RCHO $\rightarrow$ RC$\equiv$CH or RC$\equiv$CR')", *Tetrahedron Lett.*, 1972, 36, 3769–3772.

Ferguson, T.A. et al., "Two integrin–binding peptides abrogate T cell–mediated immune responses in vivo",*Proc. Natl. Acad. Sci. USA*, 1991, 88, 8072–8076.

Holzmann, B. et al., "Peyer's patch–specific lymphocyte homing receptors consist of a VLA–4–like a chain associated with either of two integrin $\beta$ chains, one of which is novel", *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design,", *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1", *J. Immunol.*, 1992, 149(10), 3394–3402.

Lei, H. et al., "Efficient Synthesis of a Phosphinate Bis–Amino Acid and Its Use in the Construction of Amphiphilic Peptides", *J. Org. Chem.*, 1994, 59, 4206–4210.

Li, Z. et al., "Effect of an anti–Mo1 MAb on ozone–induced airway inflammation and airway hyperresponsiveness in dogs", *Am. J. Physiol.*, 1992, 263(6 Pt 1), L723–726.

Marlin, S.D. et al., "LFA–1 Immunodefiency Disease", *J. Exp. Med.*, 1986, 164, 855–867.

Nagasawa, H.T. et al., "$\beta$–Substituted Cysteines as Sequestering Agents for Ethanol–Derived Acetaldehyde in Vivo", *J. Med. Chem.*, 1987, 30, 1373–1378.

Osborne, L., "Leukoctye Adhesion to Endothelium in Inflammation", *Cell*, 1990, 62, 3–6.

Osborn, L. et al., "Direct Expresssion Cloning of Vascular Cell Adhesion Molecule 1, a Cytokine–Induced Endothelial Protein that Binds to Lymphocytes", *Cell*, 1989, 59, 1203–1211.

Podolsky, D.K. et al., "Attenuation of Colitis in the Cotton–top Tamarian by Anti–$\alpha$4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Integrins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculation and Leukocyte Emigration: The Multistep Paradigm", *Cell*, 1994, 76, 301–314.

Vanderslice, P. et al., "A Cyclic Hexapeptide is a Potent Antagonist of $\alpha$4 Integrins", *J. Immunol.*, 1997, 158, 1710–1718.

Yang, X., "A predominant role of integrin $\alpha$4 in the spontaneous development of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies against $\alpha 4\beta 1$ integrin", *Nature*, 1992, 356, 63–66.

WPI/Derwent No. XP–002976854, Japanese Patent No. JP 04 193 895 A (Ajinomoto, K.K.), Jul. 13, 1992, DW9234, 1 Page, Abstract Only.

WPI/Derwent No. XP–002076855, Japanese Patent No. JP 56 049 373 A (Dainippon Pharm Co Ltd), May 2, 1981, DW8125, 1 Page, Abstract Only.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only 1 page).

Frank, R., et al., "Extremely mild reagent for Boc deprotection," *J. Chem. Commun.* (Cambridge), 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibodies," *Ger. Offen.*, 41 pages, doc. No. 83–97276 (abstract only, 5 pages).

Masuda, T., *Jpn. Kodai Tokkyo Koho*, 22 pages, doc. No. 115:280022 (abstract only, 1 page).

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho*, 33 pages, doc. No. 115:183296 (abstract only, 2 pages).

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026, doc. No. 123:221511 (abstract only, 4 pages).

"Cephalosporins," *Jpn. Kokai Tokkyo Koho*, 40 pages, doc. No. 99:5433 (abstract only, 2 pages).

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Ŝavrda, J., "CIS–TRANS isomerism of N–ACYL derivatives of proline and its analogues, linear peptides with CIS peptide bonds," *Proc. 14<sup>th</sup> European Peptide Symposium*, Loffet, A. (ed.), 1976, 653–656.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Keenan, R.M. et al., "Discovery of Potent Nonpeptide Vitronectin Receptor ($av\beta_3$) Antagonists," *J. Med. Chem.*, 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo [3,4–d]–1,3–benzodiazepin–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts*, 1968, 68(25), Abstract No. 114926r, 1 page.

Yanagisawa, H. et al., WO 97/37970, "Preparation of phenylalkylcarboxylic acid derivatives lowering blood sugar level," *Chemical Abstracts*, 1997, Abstract 127:307307, 4 pages.

Bach, et al., "Anomalous optical rotation and circular dichroism of N–thioacylated.alpha.–amino acids and deriva," *Acta Chem. Scand.*, 1996, 20(10), 2781–2794.

Barrett, G.C., "Circulation dichroism of N–thiobenzoly–1–α–amino acids. III. Their cicular dichroism through the near–ultraviolent wavelength range," *J. Chem. Soc.*, 1967, Section C, 1–5.

*Chemical Abstracts*, "N–[4–Thiazolidinyl)carbonyl]amino acid derivatives," 1981, 95(19), Abstract No. 169173f, 1 page.

Cornforth, J.W., "Oxazoles and Oxazolones," *Chem. Penicillin*, Princeton Book Review, 1949, pp. 688, 799, and 800.

Fu, H. et al., "Preliminary study on synthesis and antitumor activity in vitro of derivatives of timonacic," *Chemically Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,",*J. Prakt. Chem.*, 1996, 338(3), 251–256.

Jaynes, B.H. et al., "Synthesis and In Vivo Antibacterial Activity of Hygromycin a Analogs Modified at the $C_4$' Aryl Position," *Bioorg. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Schultz, Von O.–E. et al., "Analogos of nuleic acid based as antimetabolites," *Arzneimittel Forschung. Drug Res.*, 1967, 17(8), 1060–1064 (English summary included).

Tsunematsu, H. et al., "Hydrolysis of phenylthiazolones of p–guanidinophenylalanine and arginine by trypsin and related enzymes," *J. Biochem.*, 1983, 94(4), 1119–1125.

Whitlock, B.J. et al., "Structure and synthesis of lathyrine," *J. Org. Chem.*, 1965, 30, 115–118.

\* cited by examiner

CINNAMIC ACID DERIVATIVES

This invention relates to a series of cinnamic acid derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed $\alpha 4\beta 1$ consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the $\alpha 4$ chain which can pair with two different beta chains $\beta 1$ and $\beta 7$ [Sonnenberg, A. ibid]. The $\beta 4\beta 1$ pairing occurs on many circulating leukocytes (for example lymphocytes, monocytes and eosinophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between $\beta 4\beta 1$ and ligands on other cells and the extracellular matrix plays an important role in leukocyte migration and activation [Yednock, T. A. et al, Nature, 356, 63, (1992); Podolsky, D. K. etda. J. Clin. Invest. 92, 373, (1993); Abraham, W. M. et al. J. Clin. Invest. 93, 776, (1994)].

The integrin generated by the pairing of $\alpha 4$ and $\beta 7$ has been termed LPAM-1 [Holzmann, B and Weissman, I. EMBO J. 8, 1735, (1989)] and like $\alpha 4\beta 1$, binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important at sites of inflammation outside of mucosal tissue [Yang, X-D. et al, PNAS, 91, 12604 (1994)].

Regions of the peptide sequence recognised by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha\beta 7$ recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6 2495, (1996); Vanderslice, P. J. Immunol. 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of $\alpha 4$ integrins. Members of the group are able to inhibit $\alpha 4$ integrins such as $\alpha 4\beta 1$ and/or $\alpha 4\beta 7$ at concentrations at which they generally have no or minimal inhibitory action on a integrins of other subgroups. The compounds are thus of use in medicine, for example in the prophylaxis and treatment of immune or inflammatory disorders as described hereinafter.

Thus according to one aspect of the invention we provide a compound of formula (1)

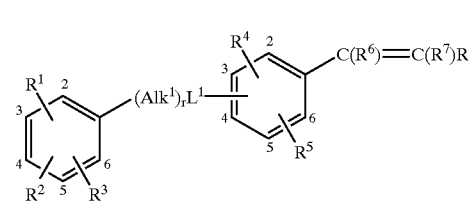

wherein $R^1$, $R^2$ and $R^3$ which may be the same or different is each an atom or group —$L^2(Alk^2)_tL^3(R^8)_u$ in which $L^2$ and $L^3$ which may be the same or different is each a covalent bond or a linker atom or group, t is zero or the integer 1, u is zero or an integer 1, 2 or 3, $Alk^2$ is an aliphatic or heteroaliphatic chain and $R^8$ is a hydrogen or halogen atom or a group selected from alkyl, —$OR^9$ [where $R^9$ is a hydrogen atom or an optionally substituted alkyl group], —$SR^9$, —$NR^9R^{10}$ [where $R^{10}$ is as just defined for $R^9$ and may be the same or different], —NO$_2$, —CN, —CO$_2$R$^9$, —OCO$_2$R$^9$, —CONR$^9$R$^{10}$, —OCONR$^9$R$^{10}$, —CSNR$^9$R$^{10}$, —COR$^9$, —OCOR$^9$, —N(R$^9$)COR$^{10}$, —N(R$^9$)CSR$^{10}$, —SO$_2$N(R$^9$)(R$^{10}$), —N(R$^9$)SO$_2$R$^{10}$, —N(R$^9$)CON(R$^{10}$)(R$^{11}$), [where R$^{11}$ is a hydrogen atom or an optionally substituted alkyl group] —N(R$^9$)CSN(R$^{10}$)(R$^{11}$) or —N(R$^9$)SO$_2$N(R$^{10}$)(R$^{11}$) provided that when one of R$^1$, R$^2$ or R$^3$ is at the 3-position of the phenyl ring it is an atom or group —L$^2$(Alk$^2$),L$^3$(R$^8$)$_u$ in which R$^8$ is as just defined other than a —N(R$^9$)CON(R$^{10}$)(R$^{11}$) or —N(R$^9$)CSN(R$^{10}$)(R$^{11}$)group;

Alk$^1$ is an optionally substituted aliphatic or heteroaliphatic chain;

L$^1$ is a covalent bond or a linker atom or group;

R$^4$ and R$^5$, which may be the same or different, is each a hydrogen or halogen atom or an alkyl, alkoxy, hydroxy or nitro group;

R$^6$ and R$^7$, which may be the same or different is each an atom or group —L$^2$(Alk$^2$),L$^3$R$^{12}$ in which L$^2$, L$^3$, Alk$^2$ and t are as previously defined and R$^{12}$ is a hydrogen or halogen atom or an —OR$^9$, —NR$^9$R$^{10}$, —NO$^2$, —CN, —CO$_2$R$^9$, —CONR$^9$R$^{10}$, —COR$^9$, —N(R$^9$)COR$^{10}$, —N(R$^9$)CSR$^{10}$, —SO$_2$N(R$^9$)(R$^{10}$), —N(R$^9$)SO$_2$R$^9$, —N(R$^9$)CON(R$^{10}$)(R$^{11}$), —N(R$^9$)CSN(R$^{10}$)(R$^{11}$), —N(R$^9$)SO$_2$N(R$^{10}$)(R$^{11}$), or an optionally substituted aliphatic, heteroaliphatic, cycloaliphatic, heterocycloaliphatic, aromatic or heteroaromatic group provided that R$^6$ and R$^7$ are not both hydrogen atoms and when R$^7$ is a hydrogen atom then R$^4$ and R$^5$ is each a hydrogen or halogen atom or an alkyl, alkoxy or nitro group;

r is zero or the integer 1;

R is a carboxylic acid (—CO$_2$H) or a derivative thereof; and the salts, solvates, hydrates and N-oxides thereof, for use in modulating cell adhesion.

It will be appreciated that compounds of formula (1) exist as geometric isomers (E or Z isomers). The compounds may also have one or more chiral centres, and exist as enantiomers or diastereomers. The invention is to be understood to extend to all such geometric isomers, enantiomers, diastereomers and mixtures thereof, including racemates. Formula (1) and the formulae hereinafter are intended to represent all individual isomers and mixtures thereof, unless stated or shown otherwise.

In the compounds of formula (1), derivatives of the carboxylic acid group R include carboxylic acid esters and amides. Particular esters and amides include —CO$_2$Alk$^5$ and —CONR$^9$R$^{10}$ groups as described herein.

Particular compounds of formula (1) form a further feature of the invention and in another aspect we therefore provide a compound of formula (1a):

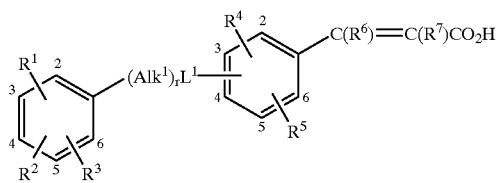

(1a)

wherein R$^1$, R$^2$, R$^3$, Alk$^1$, r, L$^1$, R$^4$, R$^5$, R$^6$ and R$^7$ are as defined for formula (1) [including the provisos stated therein] and the salts, solvates, hydrates and N-oxides thereof.

When in the compounds of formulae (1) and (1a) L$^1$ and/or L$^2$ is present as a linker atom or group it may be any divalent linking atom or group. Particular examples include —O— or —S— atoms or —C(O)—, —C(O)O—, —C(S)—, —S(O)—, —S(O)$_2$—, —N(R$^{13}$)— [where R$^{13}$ is a hydrogen atom or an optionally substituted alkyl group], —CON(R$^{13}$)—, —OC(O)N(R$^{13}$)—, —CSN(R$^{13}$)—, —N(R$^{13}$)CO—, —N(R$^{13}$)C(O)O—, —N(R$^{13}$)CS—, —S(O)$_2$N(R$^{13}$)—, —N(R$^{13}$)S(O)$_2$—, —N(R$^{13}$)CON(R$^{13}$)—, —N(R$^{13}$)CSN(R$^{13}$)—, or —N(R$^{13}$)SO$_2$N(R$^{13}$)— groups. Where the linker group contains two R$^{13}$ substituents, these may be the same or different.

When R$^4$, R$^5$, R$^8$, R$^9$, R$^{10}$, R$^{11}$ and/or R$^{13}$ in the compounds of formulae (1) or (1a) is an optionally substituted alkyl group it may be a straight or branched C$_{1-6}$alkyl group, e.g. a C$_{1-3}$alkyl group such as a methyl or ethyl group. Optional substituents which may be present on such groups include for example one, two or three substituents which may be the same or different selected from halogen atoms, for example fluorine, chlorine, bromine or iodine atoms, or hydroxy or C$_{1-6}$alkoxy e.g. methoxy or ethoxy groups.

Alkoxy groups represented by R$^4$ and/or R$^5$ in compounds of formulae (1) or (1a) include C$_{1-6}$alkoxy groups such as methoxy or ethoxy groups. Halogen atoms represented by R$^4$ and/or R$^5$ include fluorine, chlorine, bromine, or iodine atoms.

When Alk$^1$ in compounds of formulae (1) or (1a) is an optionally substituted aliphatic chain it may be an optionally substituted C$_{1-10}$ aliphatic chain. Particular examples include optionally substituted straight or branched chain C$_{1-6}$ alkyl, C$_{2-6}$ alkenyl, or C$_{2-6}$ alkynyl chains.

Heteroaliphatic chains represented by Alk$^1$ include the aliphatic chains just described but with each chain additionally containing one, two, three or four heteroatoms or heteroatom-containing groups. Particular heteroatoms or groups include atoms or groups L$^3$ where L$^3$ is as defined above for L$^1$ when L$^1$ is a linker atom or group. Each L$^3$ atom or group may interrupt the aliphatic chain, or may be positioned at its terminal carbon atom to connect the chain to an adjoining atom or group.

Particular examples of aliphatic chains represented by Alk$^1$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^3$ to form an optionally substituted heteroaliphatic chain. Particular examples include optionally substituted —L$^3$CH$_2$—, —CH$_2$L$^3$CH$_2$—, —L$^3$(CH$_2$)$_2$—, —CH$_2$L$^3$(CH$_2$)$_2$—, —(CH$_2$)$_2$L$^3$CH$_2$—, —L$^3$(CH$_2$)$_3$— and —(CH$_2$)$_2$L$^3$(CH$_2$)$_2$— chains. The optional substituents which may be present on aliphatic or heteroaliphatic chains represented by Alk$^1$ include one, two, three or more substituents where each substituent may be the same or different and is selected from halogen atoms, e.g. fluorine, chlorine, bromine or iodine atoms, or C$_{1-6}$alkoxy, e.g. methoxy or ethoxy, thiol, C$_{1-6}$alkylthio e.g. methylthio or ethylthio, amino or substituted amino groups. Substituted amino groups include —NHR$^{14}$ and —N(R$^{14}$)$_2$ groups where R$^{14}$ is an optionally substituted straight or branched alkyl group as defined above for R$^{13}$. Where two R$^{14}$ groups are present these may be the same or different. Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$— —CH$_2$CH(CF$_3$)—, —CH$_2$C(CF$_3$)$_2$—, —CH(CF$_3$)— and —C(CF$_3$)$_2$CH$_2$.

When Alk$^2$ is present in the compounds of formulae (1) or (1a) as an aliphatic or heteroaliphatic chain it may be for example any of the above-mentioned C$_{1-10}$aliphatic or heteroaliphatic chains described for Alk$^1$.

Halogen atoms represented by R$^8$ and/or R$^{12}$ include fluorine, chlorine, bromine, or iodine atoms.

When R$^{12}$ is present in compounds of formulae (1) or (1a) as an optionally substituted aliphatic or heteroaliphatic group it may be an aliphatic or heteroaliphatic group equivalent to the aliphatic or heteroaliphatic chain just described for Alk$^1$. Each aliphatic or heteroaliphatic group may be optionally substituted by one, two, three or more substituents where each substituent may be the same or different and is selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio e.g. methylthio or ethylthio, —NH$_2$ or substituted amino such as —NHR$^{14}$ or —N(R$^{14}$)$_2$ as described above.

Optionally substituted cycloaliphatic groups represented by R$^{12}$ include optionally substituted C$_{3-10}$ cycloaliphatic groups. Particular examples include optionally substituted C$_{3-10}$cycloalkyl, e.g. C$_{3-7}$cycloalkyl or C$_{3-10}$ cycloalkenyl e.g. C$_{3-7}$cycloalkenyl groups.

Optionally substituted heterocycloaliphatic groups represented by R$^{12}$ include the optionally substituted cycloaliphatic groups just described for R$^{12}$ but with each group additionally containing one, two, three or four heteroatoms or heteroatom-containing groups L$^4$ where L$^4$ is as defined above for L$^1$ when L$^1$ is a linker atom or group.

Particular examples of R$^{12}$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, isoxazinyl, oxathiazinyl, e.g. 1,2,5 or 1,2,6-oxathiazinyl, or 1,3,5-oxadiazinyl groups.

The optional substituents which may be present on the R$^{12}$ cycloaliphatic, or heterocycloaliphatic groups include one, two, three or more substituents each represented by R$^{15}$ in which R$^{15}$ is as defined above. Additionally, when R$^{12}$ is a heterocycloaliphatic group containing one or more nitrogen atoms each nitrogen atom may be optionally substituted by a group —(L$^5$)$_p$(Alk$^3$)$_q$R$^{15}$ in which L$^5$ is —C(O)—, —C(O)O—, —C(S)—, —S(O)$_2$—, —CON(R$^{13}$)—, —CSN (R$^{13}$)—, —SON(R$^{13}$)— or SO$_2$N(R$^{13}$)—; p is zero or an integer 1; Alk$^3$ is an optionally substituted aliphatic or heteroaliphatic chain; q is zero or an integer 1; and R$^{15}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^3$ include those chains described above for Alk$^1$.

Optionally substituted cycloaliphatic or heterocycloaliphatic groups represented by R$^{15}$ include those groups just described for R$^{12}$. Optional substituents which may be present on these groups include those described above in relation to R$^{12}$ alkyl and heteroalkyl groups.

Optionally substituted polycycloaliphatic groups represented by R$^{15}$ include optionally substituted C$_{7-10}$bi- or tricycloalkyl or C$_{7-10}$bi- or tricycoalkenyl groups, for example norbornyl, norbornenyl or adamantyl groups. Polyheterocycloaliphatic groups include the polycycloalkyl groups just mentioned but with each group additionally containing one, two, three or four atoms or groups selected from those atoms and groups described above for L$^1$. Optional substituents which may be present on the polycycloaliphatic or polyheterocycloaliphatic groups include those just described for R$^{15}$ cycloalkiphatic groups.

Optionally substituted aromatic or heteroaromatic groups represented by R$^{15}$ included those aromatic and heteroaromatic groups generally and specifically described below for the group R$^{12}$.

Optionally substituted aromatic groups represented by the group R$^{12}$ in compounds of the invention include for example monocyclic or bicyclic fused ring C$_{6-12}$ aromatic groups, such as phenyl, 1- or 2-naphthyl, 1- or 2-tetrahydronaphthyl, indanyl or indenyl groups, optionally substituted by one, two, three or more R$^{16}$ atoms or groups as defined below.

Optionally substituted heteroaromatic groups, represented by the group R$^{12}$ include for example optionally substituted C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include optionally substituted pyrrolyl, furyl, thienyl, imidazolyl, N-C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by R$^{12}$ include one, two, three or more substituents, each selected from an atom or group R$^{17}$ in which R$^{17}$ is —R$^{17a}$ or -Alk$^4$(R$^{17a}$)$_m$, where R$^{17a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{18}$ [where R$^{18}$ is an -Alk$^3$(R$^{17a}$)$_m$, aryl or heteroaryl group], —CSR$^{18}$, —SO$_3$H, —SO$_2$R$^{18}$ —SO$_2$NH$_2$, —SO$_2$NHR$^{18}$ SO$_2$N(R$^{18}$)$_2$, —CONH$_2$, —CSNH$_2$, —CONHR$^{18}$, —CSNHR$^{18}$, —CON

[R$^{18}$]$_2$, —CSN(R$^{18}$)$_2$, —N(R$^{13}$)SO$_2$R$^{18}$, —N(SO$_2$R$^{18}$)$_2$, —NH(R$^{13}$)SO$_2$NH$_2$, —N(R$^{13}$)SO$_2$NHR$^{18}$, —N(R$^{13}$)SO$_2$N(R$^{18}$)$_2$, —N(R$^{13}$)COR$^{18}$, —N(R$^{13}$)CON(R$^{18}$)$_2$, —N(R$^{13}$)CSN(R$^{18}$)$_2$, —N(R$^{13}$)CSR$^{18}$, —N(R$^{13}$)C(O)OR$^{18}$, —SO$_2$NHet$^1$ [where —NHet$^1$ is an optionally substituted C$_{5-7}$cyclicamino group optionally containing one or more other —O— or —S— atoms or —N(R$^{13}$)—, —C(O)— or —C(S)— groups], —CONHet$^1$, —CSNHet$^1$, —N(R$^{13}$)SO$_2$NHet$^1$, —N(R$^{13}$)CONHet$^1$, —N(R$^{13}$)CSNHet$^1$, —SO$_2$N(R$^{13}$)Het$^2$ [where Het$^2$ is an optionally substituted monocyclic C$_{5-7}$carbocyclic group optionally containing one or more —O— or —S— atoms or —N(R$^{13}$)—, —C(O)— or —C(S)— groups], —CON(R$^{13}$)Het$^2$, —CSN(R$^{13}$)Het$^2$, —N(R$^{13}$)CON(R$^{13}$)Het$^2$, —N(R$^{13}$)CSN(R$^{13}$)Het$^2$, aryl or heteroaryl group; Alk$^4$ is a straight or branched C$_{1-6}$alkylene, C$_{2-6}$alkenylene or C$_{2-6}$alkynylene chain, optionally interrupted by one, two or three —O— or —S— atoms or —S(O)$_n$ [where n is an integer 1 or 2] or —N(R$^{19}$)— groups [where R$^{19}$ is a hydrogen atom or C$_{1-6}$alkyl, e.g. methyl or ethyl group]; and m is zero or an integer 1, 2 or 3. It will be appreciated that when two R$^{13}$ or R$^{18}$ groups are present in one of the above substituents, the R$^{13}$ or R$^{18}$ groups may be the same or different.

When in the group -Alk$^4$(R$^{17a}$)$_m$ m is an integer 1, 2 or 3, it is to be understood that the substituent or substituents R$^{17a}$ may be present on any suitable carbon atom in -Alk$^4$. Where more than one R$^{17a}$ substituent is present these may be the same or different and may be present on the same or different atom in -Alk$^4$. Clearly, when m is zero and no substituent R$^{17a}$ is present the alkylene, alkenylene or alkynylene chain represented by Alk$^4$ becomes an alkyl, alkenyl or alkynyl group.

When R$^{17a}$ is a substituted amino group it may be for example a group —NHR$^{18}$ [where R$^{18}$ is as defined above] or a group —N(R$^{18}$)$_2$ wherein each R$^{18}$ group is the same or different.

When R$^{17a}$ is a halogen atom it may be for example a fluorine, chlorine, bromine, or iodine atom.

When R$^{17a}$ is a substituted hydroxyl or substituted thiol group it may be for example a group —OR$^{18}$ or a —SR$^{18}$ or —SC(=NH)NH$_2$ group respectively.

Esterified carboxyl groups represented by the group R$^{17a}$ include groups of formula —CO$_2$Alk$^5$ wherein Alk$^5$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyl-oxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^4$ group include R$^{17a}$ substituents described above.

When Alk$^4$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^{13}$)— groups.

Aryl or heteroaryl groups represented by the groups R$^{17a}$ or R$^{18}$ include mono- or bicyclic optionally substituted C$_{6-12}$ aromatic or C$_{1-9}$ heteroaromatic groups as described above for the group R$^{12}$. The aromatic and heteroaromatic groups may be attached to the remainder of the compound of formula (1) by any carbon or hetero e.g. nitrogen atom as appropriate.

When —NHet$^1$ or —Het$^2$ forms part of a substituent R$^{17}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or —Het$^2$ include those R$^8$ substituents described above.

Particularly useful atoms or groups represented by R$^{17}$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrrolyl. furyl, thiazolyl, or thienyl, C$_{1-6}$alkylamino, e.g. methylamino or ethylamino, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, isopropylaminoethoxy, or dimethylaminopropoxy, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^5$ [where Alk$^5$ is as defined above], C$_{1-6}$ alkanoyl e.g. acetyl, optionally substituted benzoyl, thiol (—SH), thioC$_{1-6}$alkyl, e.g. thiomethyl or thioethyl, —SC(=NH)NH$_2$, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocarbonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g.

ethylaminothiocarbonylmethylamino, —CONHC(═NH)NH$_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, benzylthio, pyridylmethylthio or thiazolylmethylthio groups.

Where desired, two $R^{17}$ substituents may be linked together to form a cyclic group such as a cyclic ether, e.g. a $C_{1-6}$alkylenedioxy group such as methylenedioxy or ethylenedioxy.

It will be appreciated that where two or more $R^{17}$ substituents are present, these need not necessarily be the same atoms and/or groups. In general, the substituent(s) may be present at any available ring position in the aromatic or heteroaromatic group represented by $R^{12}$.

The presence of certain substituents in the compounds of formula (1) may enable salts of the compounds to be formed. Suitable salts include pharmaceutically acceptable salts, for example acid addition salts derived from inorganic or organic acids. and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

As noted above, the compounds of formulae (1) or (1a) may exist as geometric isomers. Thus, for example, one set of isomeric pairs of compounds of formula (1) is that wherein the $R^6$ and $R^7$ groups are in a cis:

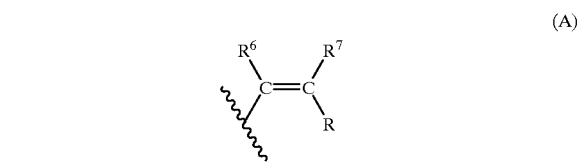

(A)

or trans relationship:

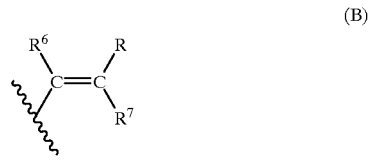

(B)

Similarly, cis and trans isomers may exist in compounds of formula (1a):

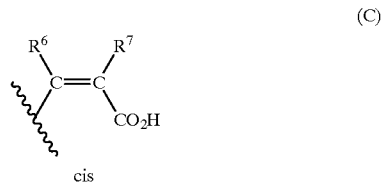

(C)

cis or

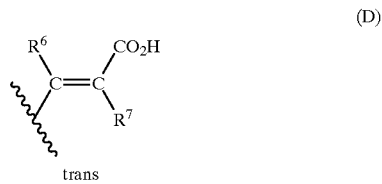

(D)

trans

Although as explained previously the invention extends and relates to all geometric isomers of compounds of formlae (1) and (1a), certain of these isomers have particularly advantageous pharmacokinetic properties which makes them especially suitable for use in medicine. Thus, generally $R^6$ and $R^7$ are preferably in a trans relationship to each other [(B) or (D) above] in the compounds of formulae (1) and (1a).

When each of $R^1$, $R^2$ and $R^3$ in compounds of formulae (1) or (1a) is a substituent other than a hydrogen atom these groups may be positioned in any arrangement at the 2-, 3-, 4-, 5- or 6-positions of the phenyl ring, for example to form 2,3,6- or 2,4,6-trisubstituted phenyl groups.

When one of $R^1$, $R^2$ and $R^3$ is a hydrogen atom and each of the other two is a halogen atom or one of the other groups described above, then the resulting disubstituted phenyl groups are preferably 2,4- or, especially, 2,6-disubstituted phenyl groups.

A particularly useful group of compounds according to the invention has the formula (2):

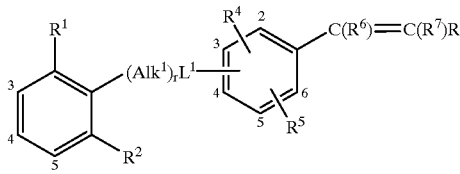

(2)

wherein
$R^1$ and $R^2$, which may be the same or different is each an atom or group —$L^2(Alk^2)_tL^3(R^8)_u$ in which $L^2$, $Alk^2$, t, $L^3$, $R^8$ and u are as defined for formula (1) provided that $R^1$ and $R^2$ are not both hydrogen atoms;

$Alk^1$, r, $L^1$, $R^4$, $R^5$, $R^7$ and R are as defined for formula (1);

$R^6$ and $R^7$, which may be the same or different is each an atom or group —$L^2(Alk^2)_tL^3R^{12}$ in which $L^2$, $L^3$, $Alk^2$ and t are as previously defined and $R^{12}$ is a hydrogen or halogen atom or an —$OR^9$, —$NR^9R^{10}$, —$NO_2$, —CN, —$CO_2R^9$, —$CONR^9R^{10}$, —$COR^9$, —$N(R^9)COR^{10}$, —$N(R^9)CSR^{10}$, —$SO_2N(R^9)(R^{10})$, —$N(R^9)SO_2R^9$, —$N(R^9)CON(R^{10})(R^{11})$, —$N(R^9)CSN(R^{10})(R^{11})$, —$N(R^9)SO_2N(R^{10})(R^{11})$, or an optionally substituted aliphatic, heteroaliphatic, cycloaliphatic, heterocycloaliphatic, aromatic or heteroaromatic group;

and the salts, solvates, hydrates and N-oxides thereof.

In the compounds of formula (2) the $R^6$ and $R^7$ substituents preferably have a trans relationship as shown in (B) above.

$R^1$ and $R^2$ in compounds of formula (2) is each preferably as described above other than a hydrogen atom. Particularly useful $R^1$ and $R^2$ substituents include halogen atoms, especially fluorine or chlorine atoms, methyl, ethyl, methoxy, ethoxy, —$CF_3$, —OH, —CN, —$NO_2$, —$NH_2$, —$NHCH_3$, —$N(CH_3)_2$, —$COCH_3$, —$SCH_3$, —$CO_2H$ or —$CO_2CH_3$ groups.

R in the compounds of formulae (1) and (2) is preferably a —$CO_2H$ group.

When present, the aliphatic chain represented by $Alk^1$ in compounds of formulae (1), (1a) and (2) is preferably a —$CH_2$— chain.

In general in compounds of formulae (1), (1a) and (2) —$(Alk^1)_rL^1$— is preferably —$CH_2O$— or —$CON(R^{13})$—, and is especially a —CONH— group. The —$(Alk^1)_rL^1$— group is preferably attached to the 4-position of the phenyl ring containing the $R^4$ and $R^5$ substituents.

In general in compounds according to the invention the group $R^6$ is preferably a hydrogen atom.

Particularly useful classes of compounds according to the invention are those wherein $R^7$ is a —$L^2R^{12}$ or —$L^2Alk^2R^{12}$ atom or group. In these classes, $L^2$ when present as a linker atom or group may especially be a —NHCO—, —NHCS— or —$NHSO_2$— group. $Alk^2$ when present may especially be a $C_{1-4}$alkylene chain. $R^{12}$ may especially be a hydrogen atom or an optionally substituted cycloaliphatic, heterocycloaliphatic, aromatic or heteroaromatic group as defined herein. Particularly useful $R^{12}$ groups of this type include optionally substitued $C_{5-7}$cycloaliphatic, especially optionally substituted cyclopentyl, optionally substituted $C_{5-7}$heterocycloaliphatic, especially optionally substituted pyrrolidinyl or thiazolidinyl, optionally substituted phenyl and optionally substituted $C_{5-7}$heteroaromatic, especially optionally substituted pyridinyl groups. Optional substituents on these groups include in particular $R^{17}$ atoms or groups where the group is an aromatic or heteroaromatic group and —$(L^5)_p(Alk^3)_qR^{15}$ groups as described earlier where the group is a nitrogen-containing heterocycloaliphatic group such as a pyrrolidinyl or thiazolidinyl group. Particularly useful —$(L^5)_p(Alk^3)_qR^{15}$ groups include —$L^5CH_2R^{15}$ groups in which $R^{15}$ is a hydrogen atom or an optionally substituted aromatic, particularly optionally substituted phenyl, or optionally substituted heteroaromatic, particularly optionally substituted pyridyl group as defined herein. In these groups $L^5$ may be as defined above, and is especially a —C(O)— group.

Particularly useful compounds according to the invention include:

N-Acetyl-D-thioproline-4-[(2,6-dichlorobenzoyl)amino]-Z-didehydrophenylalanine;

N-[(2-Chloro-3-pyridinyl)carbonyl]-O-(2,6-dichlorobenzyl)-Z-didehydro tyrosine;

N-Trimethylacetyl-4-[(2,6-dichlorobenzoyl)amino]-E-didehydrophenylalanine;

and the salts, solvates, hydrates and N-oxides thereof.

Compounds according to the invention are potent and selective inhibitors of α4 integrins. The ability of the compounds to act in this way may be simply determined by employing tests such as those described in the Examples hereinafter. In particular compounds of the invention, such as the compounds of formula (1a) herein, are advantageously selective $α4β_1$ inhibitors.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$–$R^7$ $L^1$, $Alk^1$ and r when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formulae (1a) and (2).

Thus according to a further aspect of the invention, a compound of formula (1) in which R is a —$CO_2H$ group may be obtained by hydrolysis of an ester of formula (3):

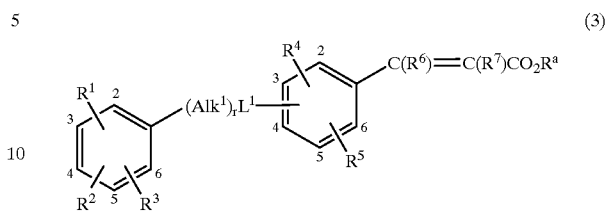

(3)

where $R^a$ is an alkyl group, for example a $C_{1-6}$alkyl group as described above.

The hydrolysis may be performed using either an acid or a base depending on the nature of $R^a$, for example an organic acid such as trifluoroacetic acid or an inorganic base such as lithium or potassium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (3) and, in general, esters of formula (1) in which R is a —$CO_2$ $Alk^5$ group may be prepared by reaction of an aldehyde or ketone of formula (4):

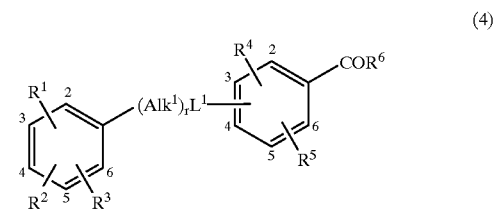

(4)

with a phosphonate $(Alk^6O)_2P(O)CH(R^7)CO_2Alk^5$, where $Alk^6$ is a $C_{1-6}$alkyl group optionally substituted by one or more fluorine atoms, in the presence of a base.

Suitable bases include organometallic bases, for example an organolithium compound such as n-butyllithium or lithium diisopropylamide, hydrides such as sodium or potassium hydride, alkoxides, such as sodium alkoxides, e.g. sodium methoxide, and cyclic amines, for example 1,8-diazabicyclo[5.4.0]undec-7-ene.

The reaction may be performed in a suitable solvent, for example a polar aprotic solvent such as an amide, e.g. N,N-dimethylformamide; or a non-polar solvent such as an ether, e.g. a cyclic ether such as tetrahydrofuran or a halogenated hydrocarbon, e.g. dichloromethane. Preferably the reaction is carried out at a low temperature for example from around −78° C. to around ambient temperature.

Intermediate phosphonates of formula $(Alk^6O)_2P(O)CH(R^7)CO_2Alk^5$ may be obtained by reaction of a halide $HalCH(R^7)CO_2Alk^5$ [where Hal is a halogen atom such as a chlorine or bromine atom] with a phosphite $P(OAlk^6)_3$. The halides $HalCH(R^7)CO_2Alk^5$ are either known compounds or may be prepared by manipulation of known compounds by the standard substitution, oxidation, reduction and/or cleavage reactions described hereinafter. In general the reaction with the phosphite $P(OAlk^6)_3$ may be carried out at any stage in the synthesis of the desired phosphonate $(Alk^6O)_2P(O)CH(R^7)CO_2Alk^5$.

Intermediate aldehydes and ketones of formula (4) are either known compounds or may be prepared by simple chemical manipulation of known compounds.

Thus, for example, the aldehydes [where $R^6$ is a hydrogen atom] may be obtained by oxidation of the corresponding alcohols [in which —$COR^6$ is a —CHOH group] using an oxidising agent such as manganese (iv) oxide in a solvent such as dichloromethane.

Intermediate ketones of formula (4) [where $R^6$ is other than a hydrogen atom] may also be obtained by oxidation of the corresponding alcohol of formula (4) using for example manganese (IV) oxide in a solvent such as dichloromethane, or by reaction of a corresponding halide [in which $COR^6$ has been replaced by a halogen atom such as a bromine or chlorine atom] by halogen-metal exchange with a base such as n-butyllithium followed by reaction with a nitrile $R^6CN$, an acid chloride $R^6COCl$ or an ester $R^6CO_2R_a$ in a solvent such as tetrahydrofuran at a low temperature e.g. around $-70°$ C. and subsequent treatment with an acid such as hydrochloric acid at around ambient temperature.

In another process, esters or amides of formula (1), for example where R is a carboxylic acid ester or amide, and in which $R^7$ is a hydrogen atom may be prepared by coupling an organopalladium compound derived from an intermediate of formula (5):

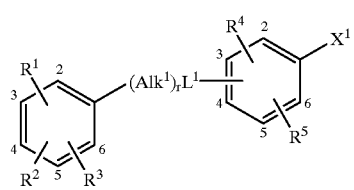
(5)

[in which $X^1$ is a halogen atom such as an iodine atom or is a trifluoromethylsulphonyloxy group] and a palladium salt with an ester or amide $R^6CHCHR$ where R is as just defined in the presence of a base.

Suitable palladium salts include palladium acetate or palladium chloride. Where palladium acetate is used the reaction for example may be carried out under phase-transfer conditions in the presence of tetra-n-butylammonium bromide and an alkali-metal base such as sodium bicarbonate in dimethylformamide. In another example, the reaction may be performed using palladium acetate or palladium chloride and a phosphine, for example a triarylphosphine such as triphenylphosphine, and a base such as triethylamine, at for example an elevated temperature and pressure.

Where desired, the starting materials in the above general coupling reaction may be varied. The reaction may thus be performed using an ester or amide of formula (1) in which R is a carboxylic acid ester or amide and $R^6$ and $R^7$ is each a hydrogen atom with a reagent $R^{6a}X^1$ in which $R^{6a}$ is an aromatic or heteroaromatic group and $X^1$ is as defined above.

Similarly the reaction may be used to generate intermediates to the final compounds described herein, for example intermediate esters of formula (3) in which $R^7$ is a hydrogen atom by using the appropriate alkene ester and a reagent $R^{6a}X^1$.

Where necessary, the intermediate aldehydes and ketones of formula (4) and the corresponding alcohols and halides described above, as well as the intermediates of formula (5) and the esters or amides $R^6CHCHR$ may be obtained from simpler aromatic or heteroaromatic compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to modify the compounds of formula (1) and the esters (3) where appropriate functional groups exist in these compounds and to generate suitable phosphonates $(Alk^6O)_2P(O)CH(R^7)CO_2Alk^5$ for example to obtain desired groups —$CH(R^7)CO_2Alk^5$ therein.

Thus compounds of the invention and intermediates thereto may be prepared by alkylation, arylation or heteroarylation. For example, compounds containing a —$L^1H$, —$L^2H$, or —$L^3H$ group (where $L^1$, $L^2$ and $L^3$ (is each a linker atom or group) may be treated with an alkylating agent:

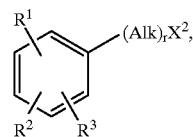

$R^{12}L^3(Alk^2)_rX^2$ or $R^{12}X^2$ in which $X^2$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a —$L^1H$, —$L^2H$ or —$L^3H$ group as defined above may be functionalised by acylation or thioacylation, for example by reaction with one of the alkylating agents just described but in which $X^2$ is replaced by a —$C(O)X^3$, $C(S)X^3$, —$N(R^9)COX^3$ or —$N(R^9)C(S)X^3$ group in which $X^3$ is a leaving atom or group as described for $X^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation or thioacylation may be carried out under the same conditions with an acid or thioacid (for example one of the alkylating agents described above in which $X^2$ is replaced by a —$CO_2H$ or —COSH group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^2$ is replaced by a —S(O)Hal or —$SO_2Hal$ group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1H$, —$L^2H$ or —$L^3H$ group as defined above may be coupled with one of the alkylation agents just described but in which X is preplaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^9$ or —$CO_2Alk^5$ in the compounds may be converted to the corresponding acid [—$CO_2H$] by acid- or base-catalysed hydrolysis depending on the nature of the groups $R^7$ or $Alk^5$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —$OR^9$ or —$OR^{18}$ groups [where $R^9$ or $R^{18}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{18}$ group (where $R^{18}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^5$ or $CO_2R^9$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^9$ group by coupling with a reagent $R^9OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group $L^1$, $L^2$ or $L^3$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystalliation and other conventional separation may also be used with intermediates or final products where it is desired to obtain a particular geometric isomer of the invention.

The following Examples illustrate the invention. All temperatures are in ° C. The following abbreviations are used:

EDC—1-(-3-dimethylaminopropyl)3-ethycarbodiimide
DMF—dimethylformamide;　　　DMSO—dimethylsulphoxide;
HOBT—1-hydroxybenzotriazole;　THF—tetrahydrofuran;
NMM—N-methylmorpholine;　　EtOAc—ethyl acetate;
MeOH—methanol;　　　　　　　LDA—lithium diisopropylamide
Ar—aryl;　　　　　　　　　　　　py—pyridine;
Me—methyl;　　　　　　　　　　DBU—1,8-diazabicyclo[5,4,O]
　　　　　　　　　　　　　　　　　undec-7-ene.

All NMR's were obtained at 300 mHz.

INTERMEDIATE 1

4-(2,6-Dichlorobenzyloxy)benzaldehyde

A suspension of 4-hydroxybenzaldehyde (19.2 g, 157.5 mmol), 2,6-dichlorobenzylbromide (36 g, 150 mmol) and potassium carbonate (22.77 g, 165 mmol) in DMF (150 ml)

was stirred at room temperature overnight. The mixture was filtered and the filtrate evaporated under reduced pressure. The residue was dissolved in ether (500 ml), and washed with aqueous NaOH (5%, 100 ml), water (100 ml) and brine (100 ml), dried ($Na_2SO_4$) and evaporated under reduced pressure. The orange crystalline solid obtained was recrystallised from diisopropylether to give the title compound as slightly orange needles (35.8 g, 85%), m.p. 70–71°. δH ($CDCl_3$) 9.91 (1H, s, CHO), 7.87 (2H, d, $J$ 8.9 Hz, ArH), 7.40–7.24 (3H, m, $ArCl_2\underline{H}$), 7.12 (2H, d, $J$ 8.7 Hz, ArH) and 5.36 (2H, s, $ArC\underline{H}_2OAr$); m/z (ESI, 60V) 281 ($\underline{M}^+$+1); Found: C, 59.76; H, 3.57. $C_{14}H_{10}O_2Cl_2$ requires C, 59.81; H, 3.59%.

INTERMEDIATE 2
2,6-Dichloro-N'-[4-(hydroxymethyl)phenvyl]benzamide 2,6-Dichlorobenzoyl chloride (3.58 ml, 25 mmol) was added to a solution of 4-aminobenzyl alcohol (3.20 g, 26 mmol) and NMM (2.96 ml, 27 mmol) in $CH_2Cl_2$ (125 ml). The mixture was stirred overnight at room temperature. Ethyl acetate (500 ml) was added to dissolve the precipitated product and the solution was washed with aqueous HCl (1M, 100 ml), dried, ($Na_2SO_4$) and evaporated under reduced pressure to give the title compound as a pale yellow solid (7.08 g, 96%). δH (DMSO-$d^6$) 10.67 (1H, s, CONH), 7.63 (2H, d, $J$ 8.5 Hz, ArH), 7.59–7.47 (3H, m, $ArCl_2H$), 7.30 (2H, d, $J$ 8.6 Hz, ArH), 4.46 (2H, s, $ArC\underline{H}_2O$) and 3.31 (1H, br s, OH), m/z (ESI, 60V) 296 ($\underline{M}^+$+1).

INTERMEDIATE 3
2,6-Dichloro-N'-(4-formylphenyl)benzamide

Manganese IV oxide (activated, <5 micron, ~85%) (25 g) was added to a suspension of Intermediate 2 (5 g, 16.9 mmol) in $CH_2Cl_2$ (200 ml). The mixture was stirred overnight at room temperature, filtered through Celite® and the filtrate evaporated under reduced pressure to give the title compound as a white solid (3.87 g, 78%). Recrystallisation from EtOAc gave white needles m.p. 211–212°. δH (DMSO-$d^6$) 11.17 (1H, s, CHO), 9.93 (1H, s, CONH), 7.94 (2H, d, $J$ 9.0 Hz, ArH), 7.90 (2H, d, $J$ 8.9 Hz, ArH) and 7.63–7.50 (3H, m, $ArCl_2H$); m/z (ESI, 60V) 294 ($\underline{M}^+$+1).

INTERMEDATE 4

N-Acetyl-D-thioproline-α-phosphonogycline Trimethyl Ester A mixture of N-(benzyloxycarbonyl)-α-phosphonoglycine trimethyl ester (5 g, 15 mmol) and palladium on charcoal (10% Pd, 500mg) in methanol (50 ml) was stirred under a hydrogen atmosphere (balloon) at room temperature for 4h. The mixture was filtered through Celite® and the filtrate evaporated under reduced pressure to give the corresponding amine. A mixture of this amine, N-acetyl thioproline (2.63 g, 15 mmol), HOBT (2.23 g, 16.5 mmol) and NMM (1.81 ml, 16.5 mmol) was dissolved in $CH_2Cl_2$ (75 ml). EDC (3.17 g, 16.5 mmol) was added and the mixture stirred overnight at room temperature. It was then diluted with $CH_2Cl_2$ (200 ml) and washed with aqueous HCl (1M, 50ml), saturated $NaHCO_3$ (50 ml) and water (50ml), dried ($Na_2SO_4$) and evaporated under reduced pressure. Purification of the residue by column chromatography ($SiO_2$; $CH_2Cl_2$/MeOH, 93:7) gave the title compound as a colourless gum (2.79 g, 53%). δH (DMSO-$d^6$) (spectrum complex due to presence of rotamers and diastereoisomers) 9.2 (br m) and 8.9 (br m) together (1H, CONH), 5.75–492 (2H, m, $2 \times CH_\alpha$), 4.74 (d, $J$ 8.8 Hz) and 4.73 (d, $J$ 9.7 Hz) and 4.53 (d, $J$ 8.6 HZ) and 4.52 (d, $J$ 8.6 Hz) and 4.32 (d. $J$ 9.7 Hz) and 4.31 (d, $J$ 9.8 Hz) together (2H, $NCH_2S$), 3.74–3.67 (several S, 9H, $CO_2Me+P(OMe)_2$), 3.49 (dd, $J$ 7.3, 11.8 Hz) and 3.35–3.26 (m) and 3.14–3.07 (m) and 2.97 (dd, $J$ 4.4, 11.9 Hz) together (2H, $CHC\underline{H}_2S$), 2.061 (s) and 2.057 (s) and 1.92 (s) and 1.91 (s) together (3H, $NCOCH_3$); m/z (ESI, 60V) 355 ($\underline{M}^+$+1).

INTERMEDIATE 5
N-(2-Chloro-3-pyridinyl)carbonyl-α-phosphonoglycine Triethyl Ester To a solution of 2-amino-triethyl(phosphonyl)acetate [prepared according to the procedure described by Shiraki, C et al in Synth. (1988) 399] (5.8 g, 24.3 mmol) in DMF (100 ml) at room temperature was added 2-chloronicotinic acid (3.82 g, 1.0 eq), NMM (5.87 ml, 2.2 eq) and HOBT (3.60 g, 1.1 eq). The resulting solution was stirred for five minutes prior to the additon of EDC hydrochloride (4.89 g, 1.05 eq). The mixture was stirred at this temperature for three hours and then partitoned between EtOAc (400 ml) and water (200 ml). The organics were separated and washed with water (5×100 ml), brine (100 ml), dried ($MgSO_4$), filtered and solvent removed in vacuo to give a crude product. This was subjected to column chromatography ($SiO_2$; eluant EtOAc) to give the title compound as a white foam (6.60 g, 72%). δH ($CDCl_3$) 8.54 (1H, dd, $J$ 1.9, 4.9 Hz), 8.10 (1H, dd, $J$ 1.9, 7.4 Hz), 7.42 (1H, br, N$\underline{H}$), 7.30 (1H, dd, $J$ 7.4, 4.9 Hz), 5.32 (1H, dd, $J$ 21.8, 8.7 Hz), 4.4–4.1 (6H, m, $3 \times OC\underline{H}_2$) and 1.55–1.40 (9H, m, $3 \times OC\underline{H}_3$). m/z (ESI, 60V) 379 ($\underline{M}^+$+1).

INTERMEDIATE 6
N-(Trimethylacetyl)-α-(phosphonoglycine Trimethyl Ester

A mixture of N-(benzyloxycarbonyl)-α-phosphonoglycine trimethyl ester (Aldrich, 5 g, 15 mmol) and palladium on charcoal (10% pd, 1.0 g) in methanol 60 ml) was stirred under a hydrogen atmosphere (balloon) at room temperature for 2 h. The mixture was filtered through Celite® and the filtrate evaporated under reduced pressure to give the corrsponding amine. This amine was dissolved in $CH_2Cl_2$ (75 ml) at 0°. NMM (1.65 ml, 15 mmol) and trimethylacetyl chloride (1.85 ml, 15 mmol) were added and the mixture stirred at room temperature overnight. The mixture was diluted with $CH_2Cl_2$ (300 ml), washed with dilute hydrochloric acid (1M, 50 ml) and saturated aqueous sodium hydrogen carbonate (50 ml), dried ($Na_2SO_4$) and evaporated under reduced pressure to give the title compound as a white waxy solid (4.0 g, 95%). δH (DMSO-$d^6$) 8.08 (1H, br d, $J$ 8.9 Hz, CONH), 5.15 (1H, dd, $J$ 23.7, 9.0 Hz, $CH_\alpha$), 3.73–3.67 (9H, m, $CO_2Me+P(OMe)_2$) and 1.14 (9H, s, $Me_3CCO$); m/z (ESI, 60V) 282 ($\underline{M}^+$+1).

EXAMPLE 1
N-Acetyl-D-thioproline-O-(2,6-dichlorobenzyl)-Z-didehydrotyrosine Methyl Ester (Isomer A)

A solution of Intermediate 4 (730 mg, 2.06 mmol) in THF (10 ml) was added dropwise to a stirred suspension of sodium hydride (60% in mineral oil, 91 mg, 2.27 mmol) in THF (5 ml) at room temperature. After 15 min a solution of Intermediate 1 (590 mg, 2.1 mmol) in THF (5 ml) was added. After 7 h the reaction mixture was quenched by the addition of water (1 ml) and the bulk of the THF was evaporated under reduced pressure. The residue was diluted with $CH_2Cl_2$ (200 ml) and washed with water (50 ml). The organic phase was dried ($Na_2SO_4$) and evaporated under reduced pressure. Column chromatography ($SiO_2$; $CH_2Cl_2$/MeOH, 95:5) gave the product as a mixture of double bond geometric isomers (76:24 determined by NMR of sample of crude mixture prior to purification). Crystallisation from ethyl acetate gave the major double bond title compound Isomer (A) as white needles (443 mg), m.p. 189–190°. (a further 175 mg was obtained as a second crop). δH (DMSO-d⁶, 390 K), 9.14 (1H, br s, CONH), 7.64 (2H, d, $J$ 8.9 Hz, ArH), 7.53–7.41 (3H, m, ArCl$_2$H), 7.34 (1H, s, C=CH), 7.07 (2H, d, $J$ 8.8 Hz, ArH), 5.34 (2H, s, Cl$_2$ArC$\underline{H}_2$O), 4.98 (1H, dd, $J$ 3.9, 7.3 Hz, CHαthiopro), 4.81 (1H, d, $J$ 9.1 Hz, NC$\underline{H}_A$H$_B$S), 4.53 (1H, d, $J$ 9.1 Hz, NCH$_A\underline{H}_B$S), 3.74 (3H, s, CO$_2$Me), 3.40 (1H, dd, $J$ 7.4, 11.4 Hz, CHC$\underline{H}_A$H$_B$S), 3.26 (1H, dd, $J$ 3.9, 11.6 Hz, CHCH$_A\underline{H}_B$S) and 2.10 (3H, s, NCOCH$_3$); m/z (ESI, 60V) 509 ($\underline{M}^+$+1).

EXAMPLE 2
N-Acetyl-D-thioproline-O-(2,6-dichlorobenzyl)-E-didehydrotyrosine Methyl Ester (Isomer B)

A solution of Intermediate 4 (515 mg, 1.45 mmol) in THF (10 ml) was added slowly to a solution of LDA (2M, 727 μl, 1.45 mmol) in THF (5 ml) at −78°. The suspension was allowed to warm slowly to 0°. A solution of Intermediate 1 (408 mg, 1.45 mmol) in THF (3 ml) was added followed by DMF (2 ml). The solution obtained was stirred at room temperature overnight. The solvents were removed under reduced pressure. The residue was dissolved in ethyl acetate (200 ml), washed with aqueous HCl (1M, 30 ml), water (30 ml) and brine (30 ml), dried (Na$_2$SO$_4$) and evaporated under reduced pressure. The crude product contained a mixture of double bond geometric isomers, Isomer A: Isomer B, 56:44 determined by ¹H NMR. Column chromatography (SiO$_2$; CH$_2$Cl$_2$/MeOH, 97:3) gave some (105 mg) of the less polar, title compound, Isomer B free from its geometric isomer. δH (CDCl$_3$) (DMSO-d⁶, 390 K), 9.49 (1H, br s, CONH), 7.53–7.40 (3H, m, ArCl$_2$H), 7.26 (2H, d, $J$ 8.4 Hz, ArH), 7.02 (2H, d, $J$ 8.8 Hz, ArH), 6.83 (1H, s, C=CH), 5.30 (2H, s, ArCH$_2$O), 4.93 (1H, dd, $J$ 3.9, 7.3 Hz, CHαthiopro), 4.80 (1H, d, $J$ 9.1 Hz, NC$\underline{H}_A$H$_B$S), 4.52 (1H, d, $J$ 9.1 Hz, NCH$_A\underline{H}_B$S), 3.65 (3H, s, CO$_2$Me), 3.39 (1H, dd, $J$ 7.3, 11.6 Hz, CHC$\underline{H}_A$H$_B$S), 3.22 (1H, dd, $J$ 3.9, 11.7 Hz, CHCH$_A\underline{H}_B$S) and 2.09 (3H, s, NCOCH$_3$); m/z (ESI, 60V) 509 ($\underline{M}^+$+1).

EXAMPLE 3
N-Acetyl-D-thioproline-4-[(2.6-dichlorobenzoyl)amino]-Z-didehydrophenylalanine Methyl Ester (Isomer A)

DBU (23 μl, 1.48 mmol) was added to a solution of Intermediate 4 (525 mg, 1.48 mmol) and Intermediate 3 (3435 mg, 1.48 mmol) in CH$_2$Cl$_2$ (15 ml). The reaction mixture was stirred overnight at room temperature, diluted with CH$_2$Cl$_2$ (200 ml), washed with aqueous HCl (1M, 30 ml), dried (Na$_2$SO$_4$) and evaporated under reduced pressure. Only one double bond isomer was detected in the crude mixture by NMR. Column chromatography (SiO$_2$; CH$_2$Cl$_2$/MeOH, 93:7) gave the title compound as a colourless foam (748 mg) and crystallisation from MeOH gave white needles (544 mg) m.p. 159–160°. δH (DMSO-d⁶, 390 K) 10.46 (1H, br s, ArCONH), 9.18 (1H, br s, CHCON$\underline{H}$), 7.68–7.63 (4H, m, ArH), 7.54–7.44 (3H, m, ArCl$_2$H), 7.34 (1H, s, C+CH), 4.99 (1H, dd, $J$ 4.0, 7.3 Hz, CHαthiopro), 4.81 (1M, d, $J$ 9.1 Hz, NC$\underline{H}_A$H$_B$S), 4.54 (1H, d, $J$ 9.1 Hz, NCH$_A\underline{H}_B$S), 3.75 (3H, s, CO$_2$Me), 3.41 (1H, dd, $J$ 7.3, 11.6 Hz, CHC$\underline{H}_A$H$_B$S), 3.26 (1H, dd, $J$ 3.0, 11.6 Hz, CHCH$_A\underline{H}_B$S) and 2.11 (3H, s, NCOCH$_3$); m/z (ESI, 60V) 522 ($\underline{M}^+$+1).

EXAMPLE 4
N-[(2-Chloro-3-pyridinyl)carbonyl]-O-(2,6-dichlorobenzyl)-Z-didehydrotyrosine Ethyl Ester (Isomer A)

DBU (150 μl, 1 mmol) was added to a solution of Intermediate 5 (380 mg, 1 mmol) and Intermediate 3 (281 mg, 1 mmol) in CH$_2$Cl$_2$ (10 ml). The reaction mixture was stirred overnight at room temperature, diluted with CH$_2$Cl$_2$ (200 ml), washed with aqueous HCl (1M, 30 ml), dried (Na$_2$SO$_4$) and evaporated under reduced pressure. Only one double bond isomer was detected by NMR in the crude reaction mixture. Column chromatography (SiO$_2$; CH$_2$Cl$_2$/MeOH, 97:3) gave the title compound as a white solid (362 mg, 72%). δH (DMSO-d⁶) 10.24 (1H, s, CONH), 8.54 (1H, dd, $J$ 1.9, 4.8 Hz, Py-4H), 7.95 (1H, dd, $J$ 1.9, 7.5 Hz, Py-6H), 7.77 (2H, d, $J$ 8.9 Hz, ArH), 7.60–7.56 (3H, m, Py-5H+2×ArCl$_2$H), 7.50–7.45 (1H, m, ArCl$_2$H), 7.44 (1H, s, C=CH), 7.15 (2H, d, $J$ 8.9 Hz, ArH), 5.29 (2H, s, ArCH$_2$O), 4.23 (2H, q, $J$ 7.1 Hz, OC$\underline{H}_2$CH$_3$) and 1.29 (3H, t, $J$ 7.1 Hz, OCH$_2$C$\underline{H}_3$); m/z (ESI, 60V) 505 ($\underline{M}^+$+1).

EXAMPLE 5
N-Acetyl-D-thioproline-O-(2,6-dichlorobenzyl)-Z-didehydrotyrosine (Isomer A)

The compound of Example 1 (382 mg, 0.75 mmol) was dissolved in a mixture of THF (7.5 ml) and water (7.5 ml). Lithium hydroxide monohydrate (35 mg, 0.83 mmol) was added and the mixture sirred overnight. The THF was evaporated under reduced pressure, the aqueous residue acidified [aqueous HCl (1M)] and extracted with CH$_2$Cl$_2$ (2×50 ml). The organic extracts were dried (Na$_2$SO$_4$) and evaporated under reduced pressure. Lyophilisation from a mixture of methanol and water gave the title compound as a fluffy white solid (352 mg, 95%). δH (DMSO-d⁶, 390 K), 9.01 (1H, br s, CONH), 7.61 (2H, d, $J$ 8.8 Hz, ArH), 7.53–7.40 (3H, m, ArCl$_2$H), 7.35 (1H, s, C=CH), 7.05 (2H, d, $J$ 8.9 Hz, ArH), 5.34 (2H, s, ArCH$_2$O), 4.98 (1H, dd, $J$ 4.0, 7.3 Hz, CHαthiopro), 4.81 (1H, d, $J$ 9.1 Hz, NC$\underline{H}_A$H$_B$S), 4.52 (1H, d, $J$ 9.1 Hz, N-CH$_A\underline{H}_B$S), 3.39 (1H, dd, $J$ 7.3, 11.7 Hz, CHC$\underline{H}_A$H$_B$S), 3.27 (1H, dd, $J$ 4.0, 11.0 Hz, CHCH$_A\underline{H}_B$S) and 2.10 (3H, s, NCOCH$_3$) (acid proton not observed), m/z (ESI, 60V) 495 ($\underline{M}^+$+1), Found: C, 52.91; H, 4.01; N, 5.52. C$_{22}$H$_{10}$N$_2$O$_5$SCl$_2$ 0.25 (H$_2$O) requires C, 52.85; H, 4.13; N, 5.60%.

EXAMPLE 6
N-Acetyl-D-thioproline-O-(2,6-dichlorobenzyl)-E-didehydrotyrosine (Isomer B)

The compound of Example 2 Isomer B (100 mg, 0.196 mmol) was dissolved in a mixture of THF (5 ml) and water (5 ml). Lithium hydroxide monohydrate (9 mg, 0.216 mmol) was added and the mixture stirred at room temperature overnight. The THF was evaporated under reduced pressure. The aqueous residue was acidified with aqueous HCl (1M) and extracted with CH$_2$Cl$_2$ (2×50 ml). The extracts were dried (Na$_2$SO$_4$) and evaporated under reduced pressure. Freeze-drying from a mixture of methanol and water gave the title compound as a fluffy white solid (84 mg, 87%). δH (DMSO-d⁶, 390 K), 9.28 (1H, br s, CONH), 7.52–7.40 (3H, m, ArCl$_2$H), 7.35 (2H, d, $J$ 8.7 Hz, ArH), 7.00 (2H, d, $J$ 8.7 Hz, ArH), 6.94 (1H, s, C=CH), 5.30 (2H, s, ArCH$_2$O), 4.95 (1H, dd, $J$ 3.9, 7.3 Hz, CHαthiapro), 4.81 (1H, d, $J$ 9.1 Hz, NC$\underline{H}_A$H$_B$S), 4.52 (1H, d, $J$ 9.1 Hz, NCH$_A\underline{H}_B$S), 3.38 (1H, dd, $J$ 7.4, 11.6 Hz, CHC$\underline{H}_A$H$_B$S), 3.24 (1H, dd, $J$ 3.9, 11.6 Hz, CHCH$_A\underline{H}_B$S) and 2.10 (3H, s, NCOCH$_3$) (no signal for acid proton observed): m/z (ESI, 60V) 495 ($\underline{M}^+$+1). Found: C, 53.07; H, 4.10; N, 5.53. C$_{22}$H$_{20}$N$_2$O$_5$SCl$_2$ requires C, 53.34; H, 4.07; N, 5.66%.

EXAMPLE 7
N-Acetyl-D-thioproline-4-[(2,6-dichlorobenzoyl)amino]-Z-didehydrophenylalanine (Isomer A)

The compound of Example 3 (435 mg, 0.833 mmol) was dissolved in a mixture of THF (10 ml), MeOH (5 ml) and water (10 ml). Lithium hydroxide monohydrate (39 mg, 0.92 mmol) was added and the mixture stirred overnight at room temperature. The organic solvents were removed under reduced pressure. The aqueous residue was acidified with aqueous HCl (1M) and the precipitate formed filtered off and washed well with water. The solid was dried under reduced pressure at 50° C. to give the title compound as a white solid (393 mg, 93%). δH (DMSO-d$^6$, 390 K) 10.44 (1H, br s, ArCONH), 9.05 (1H, br s, CHCON$\underline{H}$), 7.67–7.61 (4H, m, ArH), 4.99 (1H, dd, J 4.0, 7.3 Hz, CHαthiopro), 4.81 (1H, d, J 9.1 Hz, NC$\underline{H}_A$H$_B$S), 4.53 (1H, d, J 9.1 Hz, NCH$_A$$\underline{H}_B$S), 3.40 (1H, dd, J 7.4, 11.5 Hz, CHC$\underline{H}_A$H$_B$S), 3.27 (1H, dd, J 4.0, 11.6 Hz, CHCH$_A$$\underline{H}_B$S) and 2.11 (3H, s, COCH$_3$) (acid proton not observed); m/z (ESI, 60V) 508 ($\underline{M}^+$+1). Found: C, 57.21; H, 3.76; N, 8.18. $C_{22}H_{19}N_3O_5SCl_2$-0.8 ($H_2O$) requires C, 51.25; H, 3.87; N, 8.5%.

EXAMPLE 8

N-[(2-Chloro-3-pyridinyl)carbonyl]-O-(2,6-dichlorobenzyl)-Z-didehydro Tyrosine (Isomer A)

The compound of Example 4 (350 mg, 0.692 mmol) was dissolved in a mixture of dioxane (10 ml) and water (10 ml). Lithium hydroxide monohydrate (32 mg, 0.76 mmol) was added and the mixture stirred overnight at room temperature. The dioxane was removed under reduced pressure, and the aqueous residue was acidified with glacial acetic acid. The precipitate formed was filtered off, washed well with water and dried at 50° C. under reduced pressure to give the title compound as a white solid (214 mg, 65%). δH (DMSO-d$^6$) 12.8 (1H, v br s, CO$_2$H), 10.08 (1H, s, CONH), 8.53 (1H, dd, J 2.8, 4.7 Hz, Py-4H), 7.94 (1H, dd, J 1.8, 7.5 Hz, Py-6H), 7.75 (2H, d, J 8.8 Hz, ArH), 7.59–7.56 (3H, m, Py-5H+2×ArCl$_2$H), 7.50–7.45 (2H, m, ArCl$_2$H+C=CH), 7.13 (2H, d, J 8.8 Hz, ArH) and 5.29 (2H, s, ArCH$_2$O): m/z (ESI, 60V) 477 ($\underline{M}^+$+1). Found: C, 54.70; H, 310; N, 5.64. $C_{22}H_{15}Cl_3N_2O_4$-0.6 ($H_2O$) requires C, 54.69; H, 3.26; N, 5.80%.

EXAMPLE 9

N-Trimethylacetal-4-[(2,6-dichlorobenzoyl)amino]-Z-didehydrophenylalanine Methyl Ester DBU (451 μl, 3.0 mmol) was added to a mixture of Intermediate 3 (882 mg, 3.0 mmol) and Intermediate 6 (843 mg, 3.0 mmol) in CH$_2$Cl$_2$ (30 ml). The mixture was stirred overnight at room temperature. The precipitate formed was filtered off and washed with a small volume of CH$_2$Cl$_2$ to give the title compound as a white solid (646 mg). The filtrate was diluted with CH$_2$Cl$_2$ (100 ml), washed with dilute HCl (aqueous), dried (Na$_2$SO$_4$) and evaporated in vacuo. The solid obtained was triturated with CH$_2$Cl$_2$ and the white solid filtered off to give a second crop of the title compound (515 mg). δ$_H$ (DMSO-d$^6$) 10.91 (1H, s, ArCONH), 9.08 (1H, s, Me$_3$CCON$\underline{H}$), 7.72 (2H, d, J 8.8 Hz, ArH), 7.64 (2H, d, J 8.8 Hz, ArH), 7.61–7.48 (3H, m, Cl$_2$ArH), 7.26 (1H, s, C=CH), 3.70 (3H, s, CO$_2$Me) and 1.21 (9H, s. Me$_3$CO); m/z (ESI, 60V) 448 (MH$^+$).

EXAMPLE 10

N-Trimethylacetal-4-[(2,6-dichlorobenzoyl)amino]-Z-didehydro Phenylalanine

Lithium hydroxide monohydrate (126 mg, 3.0 mmol) was added to the compound of Example 9 (680 mg, 1.51 mmol) in a mixture of dioxane (15 ml) and water (15 ml). The mixture was stirred overnight at room temperature. The dioxane was removed in vacuo and the aqueous residue acidified with dilute HCl (aqueous). The precipitate formed was filtered off, washed with water and dried to give the title compound as a white solid (597 mg). δ$_H$ (DMSO-d$^6$) 12.45 (1H, br s, CO$_2$H), 10.89 (1H, s, ArCONH), 8.92 (1H, s, Me$_3$CONH), 7.70 (2H, d, J 8.8 Hz, ArH), 7.63–7.48 (5H, m, ArH+Cl$_2$ArH), 7.28 (1H, s, C=CH) and 1.21 (9H, s, Me$_3$CO); m/z (ESI, 60V) 435 (MH$^+$).

EXAMPLE 11

N-Trimethylacetyl-4-[(2,6-dichlorobenzoyl)amino]-E-didehydrophenylalanine Methyl Ester A solution of Intermediate 6 (843 mg, 3.0 mmol) in THF (10 ml) was added to a solution of LDA (2M, 1.5 ml, 3.0 mmol) in THF (10 ml) at −78°. The mixture was warmed to 0° and a solution of Intermediate 3 (882 mg, 3 mmol) in THF (10 ml) was added. The mixture was stirred ovrnight at room temperature, diluted with CH$_2$Cl$_2$ (300 ml), washed with dilute HCl (aqueous), dried (Na$_2$SO$_4$) and evaporated in vacuo to give the title compound as a mixture with the Z isomer. Trituration with a small volume of CH$_2$Cl$_2$ and filtration removed most of the Z isomer as a white solid. The filtrate was evaporated in vacuo and chromatography (SiO$_2$; CH$_2$Cl$_2$/MeOH, 97:3) gave a sample of the title compound (less polar isomer) free from the Z isomer (222 mg) as a colourless gum. δ$_H$ (DMSO-d$^6$) 10.80 (1H, s, ArCONH), 9.51 (1H, s, Me$_3$CCON$\underline{H}$), 7.65 (2H, d, J 8.7 Hz, ArH), 7.60–7.48 (3H, m, Cl$_2$ArH), 7.21 (2H, d, J 8.7 Hz, ArH), 6.55 (1H, s, C=CH),3.61 (3H, s, CO$_2$Me) and 1.16 (9H, s, Me$_3$C); m/z (ESI, 60V) 449 (MH$^+$).

EXAMPLE 12

N-Trimethylacetyl-4-[(2,6-dichlorobenzoyl)amino]-E-didehydrophenylalanine

Lithium hydroxide monohydrate (39 mg, 0.953 mmol) was addd to the compound of Example 11 (210 mg, 0.467 mmol) in a mixture of dioxane (5 ml) and water (5 ml). The mixture was stirred for 7 h at room temperature. The dioxane was removed in vacuo and the aqueous residue acidified with dilute HCl (aqueous). The precipitate formed was filtered off, washed with water and dried to give the title compound as an off-white solid (166 mg). δ$_H$ (DMSO-d$^6$) 12.63 (1H, br s, CO$_2$H), 10.78 (1H, s, ArCONH), 9.32 (1H, s, Me$_3$CCON$\underline{H}$), 7.62 (2H, d, J 8.7 Hz, ArH), 7.60–7.47 (3H, m, Cl$_2$ArH), 7.30 (2H, d, J 8.6 Hz, ArH), 6.55 (1H, s, C=CH) and 1.17 (9H, s, Me$_3$C); m/z (ESI, 60V) 435 (MH$^+$).

EXAMPLE 13

N-Acetyl-L-thioproline-O-benzyl-Z-didehydrotyrosine

Prepared as for the compound of Example 5 by hydrolysis of the corresponding methyl ester obtained from 4-benzyloxybenzaldehyde and the opposite enantiomer of Intermediate 4 according to the procedure of Example 1. The title compound was obtained as a white solid. δ$_H$ (DMSO-d$^6$, 400 K), 7.55 (2H, d, J 8.8 Hz, ArH), 7.45–7.31 (6H, m, ArH+CH=C), 7.00 (2H, d, J 8.8 Hz, ArH), 5.15 (2H, s, OC$\underline{H}_2$Ph), 4.97 (1H, dd, CHα), 4.80 (1H, d, J 9.1 Hz, NC$\underline{H}_A$H$_B$S), 4.50 (1H, d, J 9.2 Hz, NCH$_A$$\underline{H}_B$S), 3.38 (1H, dd, CHC$\underline{H}_A$H$_B$S), 3.27 (1H, dd, J 11.6, 4.0 Hz, CHCH$_A$$\underline{H}_B$S) and 2.09 (3H, s, COCH$_3$) (acid and amide proton not observed); m/z (ESI, 27V) 449 (MH$^+$).

EXAMPLE 14

N-Acetyl-L-thioproline-O-benzyl-E-didehydrotyrosine

Prepared in a similar manner to the compound of Example 6 by hydrolysis of the corresponding methyl ester obtained from 4-benzyloxybenzaldehyde and the opposite enantiomer of Intermediate 4 according to the procedure of Example 2. The title compound was obtained as a white solid. δ$_H$ (DMSO-d$^6$), (2 rotomeric species observed) 9.92 (br s) and 9.64 (br s) together (1H, CONH), 7.46–7.3 (7H, m, ArH), 6.93–6.85 (3H, m, CH=C+ArH), 5.09 (2H, s, OC$\underline{H}_2$Ph), 4.85 (1H, m, CHα), 4.78–4.71 (1H, m, NC$\underline{H}_A$H$_B$S), 4.56 (d, J 8.4 Hz) and 4.36 (d, J 9.7 Hz) together (1H, NCH$_A$$\underline{H}_B$S), 3.5–3.1 (4H, m, 2×CHC$\underline{H}_2$), 2.10 (s) and 2.00 (s) together (3H, COCH$_3$) (acid proton not obsserved); m/z (ESI, 15V) 427 (MH$^+$).

EXAMPLE 15

N-Acetyl-D-thioproline-4-[(2,6-dichlorobenzoyl)amino]-E-didehydrophenylalamine

Prepared in a similar manner to the compound of the Example 7 by hydrolysis of the corresponding methyl ester obtained from Intermediate 3 and Intermediate 4 according to the procedure of Example 3. $\delta_H$ (DMSO-d$^6$, 390 K), 10.29 (1H, br s, CONH), 7.57–7.40 (7H, m, ArH), 7.08 (1H, s, CH=C), 4.96 (1H., dd, $J$ 7.3, 3.8 Hz, CHα), 4.81 (1H, d, $J$ 9.1 Hz, NCH$_A$H$_B$S), 4.52 (1H, d, $J$ 9.2 Hz, NCH$_A$H$_B$S), 3.38 (1H, dd, $J$ 11.6, 7.3 Hz, CHCH$_A$H$_B$), 3.25 (1H, dd, $J$ 11.6, 3.8 Hz, CHCH$_A$H$_B$), 2.10 (3H, s, COCH$_3$) (acid proton not observed at 390 K); m/z (ESI, 60V) 508 (MH$^+$).

EXAMPLE 16

N-Acetyl-D-thioproline-4-(acetamido)-Z-didehydrophenylalanine

Prepared in a similar manner to the compound of Example 5 by hydrolysis of the corresponding methyl ester obtained from Intermediate 4 and 4-acetamidobenzaldehyde according to the procedure of Example 1. The title compound was obtained as a white solid. $\delta_H$ (DMSO-d$^6$, 390 K), 9.62 (1H, br s, CONH), 9.00 (1H, br s, CONH), 7.56 (4H, s, ArH), 7.32 (1H, s, CH=C), 4.98 (1H, dd, $J$ 7.3, 4.0 Hz, CHα), 4.81 (1H, d, $J$ 9.1 Hz, NCH$_A$H$_B$S), 4.52 (1H, d, $J$ 9.1 Hz, NCH$_A$H$_B$S), 3.39 (1H, dd, $J$ 11.5, 7.4 Hz, CHCH$_A$H$_B$), 3.27 (1H, dd, $J$ 11.5, 4.0 Hz, CHCH$_A$H$_B$), 2.10 (3H, s, COCH$_3$) and 2.06 (3H, s, COCH$_3$) (acid proton not observed at 390 K); m/z (ESI, 60V) 378 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

α$_4$β$_1$ Integrin-dependent Jurkat Cell Adhesion to VCAM-lg 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-lg diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

α$_4$β$_7$ Integrin-dependent JY Cell Adhesion to MAdCAM-lg

This assay was performed in the same manner as the α$_4$β$_1$ assay except that MAdCAM-lg (150 ng/ml) was used in place of 2d VCAM-lg and a sub-line of the β-lymphoblastoid cell-line JY was used in place of Jurkat cells. The IC$_{50}$ value for each test compound was determined as described in the α$_4$β$_1$ integrin assay.

α$_5$β$_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α$_4$β$_1$ assay above.

α$_m$β$_2$-dependent Human Polymorphonuclear Neutrophils Adhesion to plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_3$-dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220 xg for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention generally have IC$_{50}$ values in the α$_4$β$_1$ and α$_4$β$_7$ assays of 1 μM and below. In the other assays featuring α integrins of other subgroups the same compounds had IC$_{50}$ values of 50 μM and above thus demonstrating the potency and selectivity of their action against α$_4$ integrins.

What is claimed is:

1. A compound of formula (1):

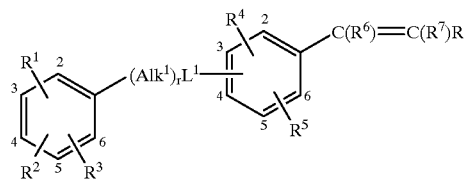

wherein

R$^1$, R$^2$ and R$^3$ which may be the same or different is each an atom or group —L$^2$(Alk$^2$)$_t$L$^3$(R$^8$)$_u$ in which L$^2$ and L$^3$ which may be the same or different is each, a covalent bond or a linker atom or group, t is zero or the integer 1, u is zero or an integer 1, 2 or 3, Alk$^2$ is an aliphatic or heteroaliphatic chain and R$^8$ is a hydrogen or halogen atom or a group selected from alkyl, —OR$^9$ (where R$^9$ is a hydrogen atom or an optionally substituted alkyl group), —SR$^9$ —NR$^9$R$^{10}$ (where R$^{10}$ is as just defined for R$^9$ and may be the same or different), —NO$_2$, —CN, —CO$_2$R$^9$, —OCO$_2$R$^9$, —CONR$^9$R$^{10}$, —OCONR$^9$R$^{10}$, —CSNR$^9$R$^{10}$, —COR$^9$, —OCOR$^9$, —N(R$^9$)COR$^{10}$, —N(R$^9$)CSR$^{10}$, —SO$_2$N(R$^9$)(R$^{10}$), —N(R$^9$)SO$_2$R$^{10}$, —N(R$^9$)CON(R$^{10}$)(R$^{11}$) (where R$^{11}$ is a hydrogen atom or an optionally substituted alkyl group), —N(R$^9$)CSN(R$^{10}$)(R$^{11}$) or —N(R$^9$)SO$_2$N(R$^{10}$)(R$^{11}$) provided that when one of R$^1$, R$^2$ or R$^3$ is at the 3-position of the phenyl ring it is an atom or group —L$^2$(Alk$^2$)$_t$L$^3$(R$^8$)$_u$, in which R$^8$ is as just defined other than a —N(R$^9$)CON(R$^{10}$)(R$^{11}$) or —N(R$^9$)CSN(R$^{10}$)(R$^{11}$) group;

Alk$^1$ is an optionally substituted aliphatic or heteroaliphatic chain;

L$^1$ is a covalent bond or a linker atom or group;

R$^4$ and R$^5$, which may be the same or different, is each a hydrogen or halogen atom or an alkyl, alkoxy, hydroxy or nitro group;

R$^6$ is an atom or group —L$^2$(Alk$^2$)$_t$L$^3$R$^{12}$ in which L$^2$, L$^3$, Alk$^2$ and t are as previously defined and R$^{12}$ is a hydrogen or halogen atom or an —OR$^9$,—NR$^9$R$^{10}$, —NO$_2$, —CN, —CO$_2$R$^9$, —CONR$^9$R$^{10}$, —COR$^9$, —N(R$^9$)COR$^{10}$, —N(R$^9$)CSR$^{10}$, —SO$_2$N(R$^9$)(R$^{10}$), —N(R$^9$)SO$_2$R$^9$, —N(R$^9$)CON(R$^{10}$)(R$^{11}$), —N(R$^9$)CSN(R$^{10}$)(R$^{11}$), —N(R$^9$)SO$_2$N(R$^{10}$)(R$^{11}$), or an optionally substituted aliphatic, heteroaliphatic, cycloaliphatic, heterocycloaliphatic, aromatic or heteroaromatic group;

R$^7$ is an —L$^2$R$^{12a}$ or —L$^2$Alk$^2$R$^{12a}$ group in which R$^{12a}$ is an optionally substituted cycloaliphatic, heterocycloaliphatic, aromatic or heteroaromatic group;

r is zero or the integer 1;

R is a carboxylic acid (—CO$_2$H) or a derivative thereof; and the salts, solvates, hydrates and N-oxides thereof, for use in modulating cell adhesion.

2. A compound of formula (1a)

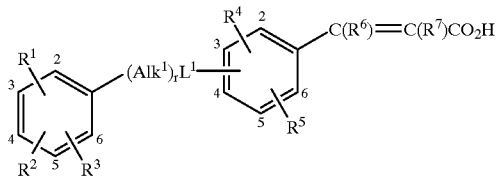

wherein

R$^1$, R$^2$ and R$^3$ which may be the same or different is each an atom or group —L$^2$(Alk$^2$)$_t$L$^3$(R$^8$)$_u$ in which L$^2$ and L$^3$ which may be the same or different is each a covalent bond or a linker atom or group, t is zero or the integer 1, u is zero or an integer 1, 2 or 3, Alk$^2$ is an aliphatic or heteroaliphatic chain and R$^8$ is a hydrogen or halogen atom or a group selected from alkyl, —OR$^9$ (where R$^9$ is a hydrogen atom or an optionally substituted alkyl group), —SR$^9$, —NR$^9$R$^{10}$ (where R$^{10}$ is as just defined for R$^9$ and may be the same or different), —NO$_2$, —CN, —CO$_2$R$^9$, —OCO$_2$R$^9$, —CONR$^9$R$^{10}$, —OCONR$^9$R$^{10}$, —CSNR$^9$R$^{10}$, —COR$^9$, —OCOR$^9$, —N(R$^9$)COR$^{10}$, —N(R$^9$)CSR$^{10}$, —SO$_2$N(R$^9$)(R$^{10}$), —N(R$^9$)SO$_2$R$^{10}$, —N(R$^9$)CON(R$^{10}$)(R$^{11}$) (where R$^{11}$ is a hydrogen atom or an optionally substituted alkyl group), —N(R$^9$)CSN(R$^{10}$)(R$^{11}$) or —N(R$^9$)SO$_2$N(R$^{10}$)(R$^{11}$) provided that when one of R$^1$, R$^2$ or R$^3$ is at the 3-position of the phenyl ring it is an atom or group —L$^2$(Alk$^2$)$_t$L$^3$(R$^8$)$_u$, in which R$^8$ is as just defined other than a —N(R$^9$)CON(R$^{10}$)(R$^{11}$) or —N(R$^9$)CSN(R$^{10}$)(R$^{11}$) group;

Alk$^1$ is an optionally substituted aliphatic or heteroaliphatic chain;

L$^1$ is a covalent bond or a linker atom or group;

R$^4$ and R$^5$, which may be the same or different is each a hydrogen or halogen atom or an alkyl, alkoxy, hydroxy or nitro group;

R$^6$ is an atom or group —L$^2$(Alk$^2$)$_t$L$^3$R$^{12}$ in which L$^2$, L$^3$, Alk$^2$ and t are as previously defined and R$^{12}$ is a hydrogen or halogen atom or an —OR$^9$, —NR$^9$R$^{10}$, —NO$_2$, —CN, —CO$_2$R$^9$, —CONR$^9$R$^{10}$, —COR$^9$, —N(R$^9$)COR$^{10}$, —N(R$^9$)CSR$^{10}$, —SO$_2$N(R$^9$)(R$^{10}$), —N(R$^9$)SO$_2$R$^9$, —N(R$^9$)CON(R$^{10}$)(R$^{11}$), —N(R$^9$)CSN(R$^{10}$)(R$^{11}$), —N(R$^9$)SO$_2$N(R$^{10}$)(R$^{11}$), or an optionally substituted aliphatic, heteroaliphatic, cycloaliphatic, heterocycloaliphatic, aromatic or heteroaromatic group;

R$^7$ is an —L$^2$R$^{12a}$ or —L$^2$Alk$^2$R$^{12a}$ group in which R$^{12a}$ is an optionally substituted cycloaliphatic, heterocycloaliphatic, aromatic or heteroaromatic group;

r is zero or the integer 1;

and the salts, solvates, hydrates and N-oxides thereof.

3. A compound according to claim 2 wherein R$^6$ and R$^7$ are in a trans relationship to each other.

4. A compound according to claim 2 wherein —(Alk$^1$)$_r$L$^1$— is a —CH$_2$O— or —CON(R$^{13}$)— group.

5. A compound according to claim 2 wherein R$^6$ is a hydrogen atom.

6. A compound according to claim 2 wherein L$^2$ is a —NHCO—, —NHCS— or —NHSO$^2$— group.

7. A compound according to claim 2 wherein Alk$^2$ is a C$_{1-4}$alkylene chain.

8. A compound according to claim 2 wherein R$^{12a}$ is an optionally substituted C$_{5-7}$cycloaliphatic, C$_{5-7}$heterocycloaliphatic, phenyl or C$_{5-7}$heteroaromatic group.

9. A compound of formula (2):

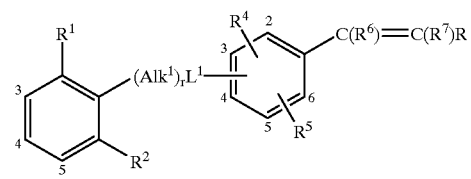

wherein

R$^1$ and R$^2$ which may be the same or different is each an atom or group —L$^2$(Alk$^2$)$_t$L$^3$(R$^8$)$_u$ in which L$^2$ and L$^3$ which may be the same or different is each a covalent bond or a linker atom or group, t is zero or the integer 1, u is zero or an integer 1, 2 or 3, Alk$^2$ is an an aliphatic or heteroaliphatic chain and R$^8$ is a hydrogen or halogen atom or a group selected from alkyl, —OR$^9$ (where R$^9$ is a hydrogen atom or an optionally substituted alkyl group), —SR$^9$, —NR$^9$R$^{10}$ (where R$^{10}$ is as just defined for R$^9$ and may be the same or different), —NO$_2$, —CN, —CO$_2$R$^9$, —OCO$_2$R$^9$, —CONR$^9$R$^{10}$, —OCONR$^9$R$^{10}$, —CSNR$^9$R$^{10}$, —COR$^9$, —OCOR$^9$, —N(R$^9$)COR$^{10}$, —N(R$^9$)CSR$^{10}$, —SO$_2$N(R$^9$)(R$^{10}$), —N(R$^9$)CON(R$^{10}$)(R$^{11}$) (where R$^{11}$ is a hydrogen atom or an optionally substituted alkyl group), —N(R$^9$)

CSN($R^{10}$)($R^{11}$) or —N($R^9$)SO$_2$N($R^{10}$)($R^{11}$) provided that $R^1$ and $R^2$ are not with hydrogen atoms;

Alk$^1$ is an optionally substituted aliphatic or heteroaliphatic chain;

L$^1$ is a covalent bond or a linker atom or group;

$R^4$ and $R^5$, which may be the same or different, is each a hydrogen or halogen atom or an alkyl, alkoxy, hydroxy or nitro group;

$R^6$ is an atom or group —L$^2$(Alk$^2$)$_t$L$^3$R$^{12}$ in which L$^2$, L$^3$, Alk$^2$ and t are as previously defined and $R^{12}$ is a hydrogen or halogen atom or an —OR$^9$, —NR$^9$R$^{10}$, —NO$_2$, —CN, —CO$_2$R$^9$, —CONR$^9$R$^{10}$, —COR$^9$, —N(R$^9$)COR$^{10}$, —N(R$^9$)CSR$^{10}$, —SO$_2$N(R$^9$)(R$^{10}$), —N(R$^9$)SO$_2$R$^9$, —N(R$^9$)CON(R$^{10}$)(R$^{11}$), —N(R$^9$)CSN(R$^{10}$)(R$^{11}$), —N(R$^9$)SO$_2$N(R$^{10}$)(R$^{11}$), or an optionally substituted aliphatic, heteroaliphatic, cycloaliphatic, heterocycloaliphatic, aromatic or heteroaromatic group;

$R^7$ is an —L$^2$R$^{12a}$ or —L$^2$Alk$^2$R$^{12a}$ group in which $R^{12a}$ is an optionally substituted cycloaliphatic, heterocycloliphatic, aromatic or heteroaromatic group;

r is zero or the integer 1;

R is a carboxylic acid (—CO$_2$H) or a derivative thereof; and the salts, solvates hydrates and N-oxides thereof.

10. A compound which is:
N-Acetyl-D-thioproline-4-[(2,6-dichlorobenzoyl)amino]-Z-didehydrophenylalanine;
N-[(2-Chloro-3-pyridinyl)carbonyl]-O-(2,6-dichlorobenzyl)-Z-didehydro tyrosine;
N-Trimethylacetyl-4-[(2,6-dichlorobenzoyl)amino]-E-didehydrophenylalanine;
and the salts, solvates, hydrates and N-oxides thereof.

11. A pharmaceutical composition comprising a compound according to claim 2 together with one or more pharmaceutically acceptable carriers, excipients or diluents.

12. A compound according to claim 10 which is N-[(2-Chloro-3-pyridinyl)carbonyl]-O-(2,6-dichlorobenzyl)-Z-didehydrotyrosine; and the salts, solvates, hydrates and N-oxides thereof.

13. A method for the prophylaxis or treatment of a disease or disorder in a mammal in which the extravasation of leukocytes plays a role, comprising administering to a mammal suffering from such a disease or disorder a therapeutically effective amount of a compound of formula (1b):

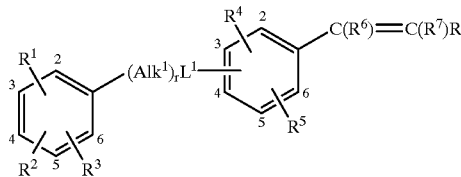

wherein $R^1$, $R^2$ and $R^3$ which may be the same or different is each an atom or group —L$^2$(Alk$^2$)$_t$L$^3$(R$^8$)$_u$ in which L$^2$ and L$^3$ which may be the same or different is each, a covalent bond or a linker atom or group, t is zero or the integer 1, u is zero or an integer 1, 2 or 3, Alk$^2$ is an aliphatic or heteroaliphatic chain and $R^8$ is a hydrogen or halogen atom or a group selected from alkyl, —OR$^9$ (where R$^9$ is a hydrogen atom or an optionally substituted alkyl group), —SR$^9$ —NR$^9$R$^{10}$ (where R$^{10}$ is as just defined for R$^9$ and may be the same or different), —NO$_2$, —CN, —CO$_2$R$^9$, —OCO$_2$R$^9$, —CONR$^9$R$^{10}$, —OCONR$^9$R$^{10}$, —CSNR$^9$R$^{10}$, —COR$^9$, —OCOR$^9$, —N(R$^9$)COR$^{10}$, —N(R$^9$)CSR$^{10}$, —SO$_2$N(R$^9$)(R$^{10}$), —N(R$^9$)SO$_2$R$^{10}$, —N(R$^9$)CON(R$^{10}$)(R$^{11}$) (where R$^{11}$ is a hydrogen atom or an optionally substituted alkyl group), —N(R$^9$)CSN(R$^{10}$)(R$^{11}$) or —N(R$^9$)SO$_2$N(R$^{10}$)(R$^{11}$) provided that when one of $R^1$, $R^2$ or $R^3$ is at the 3-position of the phenyl ring it is an atom or group —L$^2$(Alk$^2$)$_t$L$^3$(R$^8$)$_u$, in which $R^8$ is as just defined other than a —N(R$^9$)CON(R$^{10}$)(R$^{11}$) or —N(R$^9$)CSN(R$^{10}$)(R$^{11}$) group;

Alk$^1$ is an optionally substituted aliphatic or heteroaliphatic chain;

L$^1$ is a covalent bond or a linker atom or group;

$R^4$ and $R^5$, which may be the same or different, is each a hydrogen or halogen atom or an alkyl, alkoxy, hydroxy or nitro group;

$R^6$ and $R^7$ which may be the same or different is each an atom or group —L$^2$(Alk$^2$)$_t$L$^3$R$^{12}$ in which L$^2$, L$^3$, Alk$^2$ and t are as previously defined and $R^{12}$ is a hydrogen or halogen atom or an —OR$^9$, —NR$^9$R$^{10}$, —NO$_2$, —CN, —CO$_2$R$^9$, —CONR$^9$R$^{10}$, —COR$^9$, —N(R$^9$)COR$^{10}$, —N(R$^9$)CSR$^{10}$, —SO$_2$N(R$^9$)(R$^{10}$), —N(R$^9$)SO$_2$R$^9$, —N(R$^9$)CON(R$^{10}$)(R$^{11}$), —N(R$^9$)CSN(R$^{10}$)(R$^{11}$), —N(R$^9$)SO$_2$N(R$^{10}$)(R$^{11}$), or an optionally substituted aliphatic, heteroaliphatic, cycloaliphatic, heterocycloaliphatic, aromatic or heteroaromatic group; provided that $R^6$ and $R^7$ are not both hydrogen atoms; and when $R^7$ is a hydrogen atom then $R^4$ and $R^5$ is each a hydrogen or halogen atom or an alkyl alkoxy or nitro group;

r is zero or the integer 1;

R is a carboxylic acid (—CO$_2$H) or a derivative thereof; and the salts, solvates, hydrates and N-oxides thereof.

14. A method according to claim 13 wherein said disease or disorder is selected from the group consisting of inflammatory arthritis, multiple sclerosis, allograft rejection, diabetes, inflammatory dermatoses, asthma and inflammatory bowel disease.

15. A method according to claim 14 wherein said inflammatory arthritis is selected from the group consisting of rheumatoid arthritis vasculitis and polydermatomyositis.

16. A method according to claim 14 wherein said inflammatory dermatoses are selected from the group consisting of psoriasis and dermatitis.

* * * * *